(12) United States Patent
Huh et al.

(10) Patent No.: US 9,595,679 B2
(45) Date of Patent: Mar. 14, 2017

(54) ORGANIC LIGHT EMITTING DIODE

(71) Applicant: LG CHEM, LTD., Seoul (KR)

(72) Inventors: Jungoh Huh, Daejeon (KR); Dong Hoon Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/760,442

(22) PCT Filed: Oct. 21, 2014

(86) PCT No.: PCT/KR2014/009895
§ 371 (c)(1),
(2) Date: Jul. 10, 2015

(87) PCT Pub. No.: WO2016/039501
PCT Pub. Date: Mar. 17, 2016

(65) Prior Publication Data
US 2016/0276594 A1    Sep. 22, 2016

(30) Foreign Application Priority Data

Sep. 12, 2014  (KR) .......................... 10-2014-0120941

(51) Int. Cl.
*H01L 51/50* (2006.01)
*H01L 51/00* (2006.01)
*C07D 209/86* (2006.01)
*C07D 403/10* (2006.01)

(52) U.S. Cl.
CPC ........ *H01L 51/0061* (2013.01); *C07D 209/86* (2013.01); *C07D 403/10* (2013.01); *H01L 51/006* (2013.01); *H01L 51/0058* (2013.01); *H01L 51/0067* (2013.01); *H01L 51/0072* (2013.01); *H01L 51/50* (2013.01); *H01L 51/0052* (2013.01); *H01L 51/5056* (2013.01); *H01L 51/5064* (2013.01); *H01L 51/5072* (2013.01); *H01L 51/5076* (2013.01)

(58) Field of Classification Search
None
See application file for complete search history.

(56) References Cited

U.S. PATENT DOCUMENTS

| 8,865,322 | B2 | 10/2014 | Yi et al. | |
|---|---|---|---|---|
| 2005/0221124 | A1* | 10/2005 | Hwang | C07F 9/5728 428/690 |
| 2009/0160323 | A1 | 6/2009 | Nomura et al. | |
| 2013/0087768 | A1 | 4/2013 | Kim et al. | |
| 2014/0070204 | A1 | 3/2014 | Nagao et al. | |
| 2014/0183466 | A1 | 7/2014 | Lee et al. | |
| 2014/0197386 | A1 | 7/2014 | Kim et al. | |
| 2014/0225072 | A1 | 8/2014 | Kim et al. | |

FOREIGN PATENT DOCUMENTS

| CN | 1702065 A | 11/2005 |
|---|---|---|
| CN | 102372662 A | 3/2012 |
| CN | 103030585 A | 4/2013 |
| CN | 103904227 A | 7/2014 |
| JP | 200921336 A | 1/2009 |
| KR | 1020140096203 A | 8/2014 |
| KR | 1020140106740 A | 9/2014 |
| WO | 2012153725 A1 | 11/2012 |

* cited by examiner

*Primary Examiner* — Gregory Clark
(74) *Attorney, Agent, or Firm* — Dentons US LLP

(57) ABSTRACT

The present specification relates to an organic light emitting diode.

11 Claims, 1 Drawing Sheet

ORGANIC LIGHT EMITTING DIODE

This application is a National Stage Application of International Application No. PCT/KR2014/009895, filed Oct. 21, 2014, and claims the benefit of Korean Application No. 10-2014-0120941, filed Sep. 12, 2014, all of which are hereby incorporated by reference in their entirety for all purposes as if fully set forth herein.

TECHNICAL FIELD

This application claims priority to and the benefit of Korean Patent Application No. 10-2014-0120941 filed in the Korean Intellectual Property Office on Sep. 12, 2014, the entire contents of which are incorporated herein by reference.

The present specification relates to an organic light emitting diode.

BACKGROUND ART

An organic light emission phenomenon is an example of converting current into visible rays by an internal process of a specific organic molecule. A principle of the organic light emission phenomenon is as follows.

When an organic material layer is positioned between an anode and a cathode, if a voltage is applied between two electrodes, electrons and holes are respectively injected from the cathode and the anode into the organic material layer. The electrons and the holes which are injected into the organic material layer are recombined to form excitons, and light is emitted while the excitons fall down to a bottom state again. In general, an organic light emitting diode using this principle may be constituted by a cathode, an anode, and an organic material layer positioned therebetween, for example, an organic material layer including a hole injection layer, a hole transport layer, a light emitting layer, and an electron transport layer.

A material used for the organic light emitting diode is mostly a pure organic material or a complex compound where an organic material and metal form a complex, and may be classified into a hole injection material, a hole transport material, a light emitting material, an electron transport material, an electron injection material, and the like according to the purpose thereof. Herein, an organic material having a p-type property, that is, an organic material that is easily oxidized and has an electrochemically stable state during oxidation, is mostly used as the hole injection material or the hole transport material. Meanwhile, an organic material having an n-type property, that is, an organic material that is easily reduced and has an electrochemically stable state during reduction, is mostly used as the electron injection material or the electron transport material. As a light emitting layer material, a material having both p-type and n-type properties, that is, a material having a stable form in both oxidation and reduction states is preferable. Also, a material having high light emitting efficiency for converting the exciton into light when the exciton is formed is preferable.

In the art, there is a demand for developing an organic light emitting diode having high efficiency.

PRIOR ART DOCUMENT

Non-Patent Document

Applied Physics Letters 51, p. 913, 1987

DETAILED DESCRIPTION OF THE INVENTION

Technical Problem

The present specification has been made in an effort to provide an organic light emitting diode having high light emitting efficiency.

Technical Solution

An exemplary embodiment of the present specification provides an organic light emitting diode including: an anode; a cathode; a light emitting layer provided between the anode and the cathode; an organic material layer including a compound represented by the following Chemical Formula 1 and provided between the cathode and the light emitting layer; and an organic material layer including a compound represented by the following Chemical Formula 2 and provided between the anode and the light emitting layer.

[Chemical Formula 1]

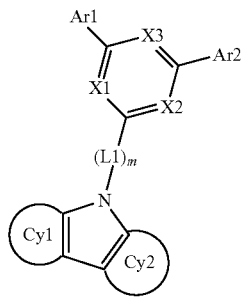

In Chemical Formula 1,

X1 to X3 are the same as or different from each other, and are each independently N or CH, at least one of X1 to X3 is N, Cy1 and Cy2 are the same as or different from each other, and are each independently a substituted or unsubstituted monocyclic or polycyclic aromatic cycle having 6 to 30 carbon atoms; or a substituted or unsubstituted monocyclic or polycyclic heterocycle having 2 to 30 carbon atoms, L1 is a substituted or unsubstituted monocyclic or polycyclic arylene group having 6 to 30 carbon atoms, m is an integer of 1 to 4, in the case where m is 2 or more, L1s are the same as or different from each other, and Ar1 and Ar2 are the same as or different from each other, and are each independently a substituted or unsubstituted monocyclic or polycyclic aryl group having 6 to 30 carbon atoms; or a substituted or unsubstituted monocyclic or polycyclic heteroaryl group having 2 to 30 carbon atoms, and

[Chemical Formula 2]

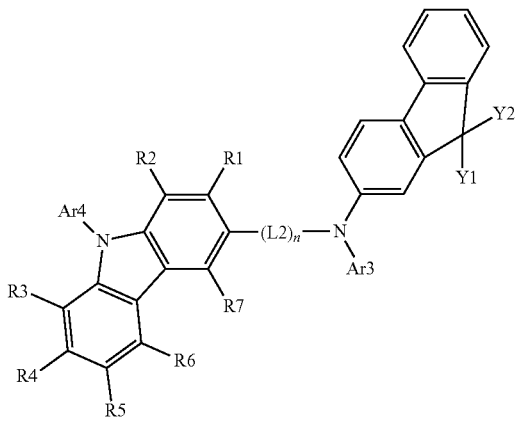

in Chemical Formula 2,

Ar3 and Ar4 are the same as or different from each other, and are hydrogen; deuterium; a substituted or unsubstituted monocyclic or polycyclic aryl group having 6 to 30 carbon atoms; or a substituted or unsubstituted monocyclic or polycyclic heteroaryl group having 2 to 30 carbon atoms, L2 is a substituted or unsubstituted monocyclic or polycyclic arylene group having 6 to 30 carbon atoms, n is an integer of 0 to 5, in the case where n is 2 or more, two or more L2s are the same as or different from each other, R1 to R7 are the same as or different from each other, and are each independently hydrogen; deuterium; a substituted or unsubstituted straight-chained or branch-chained alkyl group having 1 to 30 carbon atoms; a substituted or unsubstituted monocyclic or polycyclic aryl group having 6 to 30 carbon atoms; or a substituted or unsubstituted monocyclic or polycyclic heteroaryl group having 2 to 30 carbon atoms, or adjacent groups are bonded to each other to form a substituted or unsubstituted aromatic cycle, and Y1 and Y2 are the same as or different from each other, and are each independently hydrogen; deuterium; a substituted or unsubstituted straight-chained or branch-chained alkyl group having 1 to 30 carbon atoms; a substituted or unsubstituted monocyclic or polycyclic aryl group having 6 to 30 carbon atoms; or a substituted or unsubstituted monocyclic or polycyclic heteroaryl group having 2 to 30 carbon atoms, or Y1 and Y2 are bonded to each other to form a substituted or unsubstituted aromatic cycle.

Advantageous Effects

An organic light emitting diode according to an exemplary embodiment of the present specification provides a low driving voltage and/or high efficiency.

EXPLANATION OF REFERENCE NUMERALS AND SYMBOLS

Figure 1:
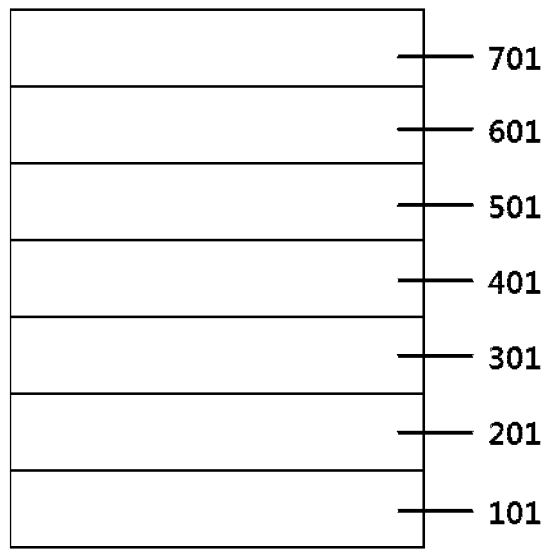
FIG. 1 illustrates an example of an organic light emitting diode according to an exemplary embodiment of the present specification.

101: Substrate
201: Anode
301: Hole transport
401: Electron blocking layer
501: Light emitting layer
601: Electron transport layer
701: Cathode
801: Electron injection layer

BEST MODE

Hereinafter, the present specification will be described in more detail.

In the present specification, unless explicitly described to the contrary, the word "comprise" and variations such as "comprises" or "comprising", will be understood to imply the inclusion of stated elements but not the exclusion of any other elements.

In the present specification, it will be understood that when an element is referred to as being positioned "on" another element, it can be directly on the other element or intervening elements may also be present between the two elements.

An organic light emitting diode according to an exemplary embodiment of the present specification includes both an organic material layer including a compound represented by Chemical Formula 1 and an organic material layer including a compound represented by Chemical Formula 2.

According to the exemplary embodiment of the present specification, the organic material layer including the compound represented by Chemical Formula 1 is an electron transport layer, an electron injection layer, or a layer simultaneously transporting and injecting electrons.

According to one exemplary embodiment of the present specification, the organic material layer including the compound represented by Chemical Formula 1 is the electron transport layer.

According to another exemplary embodiment of the present specification, an organic material layer including a compound represented by Chemical Formula 1 is an electron injection and electron transport layer. Specifically, in the organic light emitting diode according to the exemplary embodiment of the present specification, in the case where the electron injection layer is not provided, the organic material layer including the compound represented by Chemical Formula 1 may serve as both the electron injection layer and electron transport layer.

Further, according to another exemplary embodiment of the present specification, the organic light emitting diode may include only the organic material layer including the compound represented by Chemical Formula 1 between a cathode and a light emitting layer. In another exemplary embodiment, the organic light emitting diode may further include an additional organic material layer between the cathode and the organic material layer including the compound represented by Chemical Formula 1; or between the light emitting layer and the organic material layer including the compound represented by Chemical Formula 1.

According to the exemplary embodiment of the present specification, the organic material layer including the compound represented by Chemical Formula 2 is a hole transport layer.

In the related art, an organic material having an n-type property, that is, an organic material that is easily reduced and has an electrochemically stable state during reduction, is mostly used as an electron transport material. However, the organic material is electrochemically unstable during oxidation, a novel electron transport material has been continuously studied.

The compound represented by Chemical Formula 1 according to the exemplary embodiment of the present specification has a bipoar type having both a p-type property (cycle group including Cy1 and Cy2) and an n-type property (cycle group including X1 to X3), and thus has a stable state in both oxidation and reduction states. Accordingly, an effect that when an exciton is formed, light emitting efficiency of converting the exciton into light is high may be obtained.

Like the organic light emitting diode according to the exemplary embodiment of the present specification, in the case where the compound both having the bipoar property of the p-type and n-type properties and represented by Chemical Formula 1 is used as the electron transport layer and the organic material layer including the compound represented by Chemical Formula 2 is used as the hole transport layer, an increase in efficiency may be maximized.

In the exemplary embodiment of the present specification, hole mobility of the compound represented by Chemical Formula 2 is $5 \times 10^{-6}$ $cm^2/Vs$ or more. In another exemplary embodiment, hole mobility of the compound represented by Chemical Formula 2 is $5 \times 10^{-6}$ $cm^2/Vs$ or more under an electric field condition of 0.1 MV/cm. In another exemplary embodiment, hole mobility of the compound represented by Chemical Formula 2 is $10^{-6}$ $cm^2/Vs$ or more.

Hole mobility of the compound represented by Chemical Formula 2 according to the exemplary embodiment of the present specification is $5 \times 10^{-6}$ $cm^2/Vs$ or more under the electric field condition of 0.1 MV/cm, and is higher than that of an existing hole transport material. Accordingly, by increasing the number of excitons generated in the light emitting layer, high efficiency may be expected but leakage of holes to the cathode may be caused. However, in the case where the organic material layer including a heterocyclic compound represented by Chemical Formula 1 according to the exemplary embodiment of the present specification is provided between the light emitting layer and the cathode, since the compound represented by Chemical Formula 1 is the bipolar type including both the p type and the n type rather than the pure n type, the generated exciton as well as the holes leaked by Chemical Formula 2 may be effectively confined in the light emitting layer, and a stable form of the exciton, that is, hole-electron pairs against chemical attack may be maintained, a life-span as well as efficiency may be maximized.

In the present specification, hole mobility may be measured by a method used in the art. Specifically, a time of flight (TOF) method or a space charge limited current (SCLC) measurement method may be used, and the method is not limited thereto. In the present specification, in order to measure the space charge limited current (SCLC), a film thickness of the material may be set to 1000 nm or more, and thus hole mobility may be measured.

In the exemplary embodiment of the present specification, hole mobility of the compound represented by Chemical Formula 2, which is measured by the time of flight (TOF) method, is $5 \times 10^{-6}$ $cm^2/Vs$ or more.

In one exemplary embodiment of the present specification, after hexanitrile hexaazatrilephenylene is heated under the vacuum on an ITO substrate to be deposited in a thickness of 5 nm, a hole transport material represented by Chemical Formula 2 is deposited in a thickness of 200 nm, and aluminum is the deposited in a thickness of 100 nm or more to manufacture a sample. A current density ($mA/cm^2$) to a voltage of the sample may be measured to calculate hole mobility in a space charge limited current (SCLC) region.

According to the exemplary embodiment of the present specification, the organic light emitting diode further includes one or two or more layers from the group consisting of the electron injection layer and the electron transport layer between the light emitting layer and the cathode.

According to another exemplary embodiment of the present specification, the organic material layer including the compound represented by Chemical Formula 1 is the electron transport layer, and further includes the electron injection layer provided between the electron transport layer and the cathode.

According to the exemplary embodiment of the present specification, the organic light emitting diode further includes one or two or more from the group consisting of a hole injection layer, a hole transport layer, and an electron blocking layer between a light emitting layer and an anode.

According to another exemplary embodiment of the present specification, the organic material layer including the compound represented by Chemical Formula 2 is the hole transport layer, and further includes the electron blocking layer provided between the hole transport layer and the light emitting layer.

According to the exemplary embodiment of the present specification, the electron blocking layer is provided to come into contact with the light emitting layer.

In the present specification, examples of substituent groups will be described below, but are not limited thereto.

The term "substituted" means that a hydrogen atom bonded to a carbon atom of a compound is changed into another substituent group, a substitution position is not limited as long as the substitution position is a position at which the hydrogen atom is substituted, that is, a position at which the substituent group can be substituted, and in the case where two or more atoms are substituted, two or more substituent groups may be the same as or different from each other.

In the present specification, the term "substituted or unsubstituted" means that substitution is performed by one or two or more substituent groups selected from the group consisting of deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted alkenyl group; a substituted or unsubstituted amine group; a substituted or unsubstituted aryl group; and a substituted or unsubstituted heterocyclic group, substitution is performed by a substituent group where two or more substituent groups of the exemplified substituent groups are connected, or there is no substituent group. For example, the "substituent group where two or more substituent groups are connected" may be a biphenyl group. That is, the biphenyl group may be an aryl group, or may be interpreted as a substituent group where two phenyl groups are connected. The term "substituted or unsubstituted" means that substitution is performed by the substituent group where two or more substituent groups of the exemplified substituent groups are connected or there is no substitution. For example, the "substituent group where two or more substituent groups are connected" may be a biphenyl group. That is, the biphenyl group may be an aryl group, or may be interpreted as a substituent group where two phenyl groups are connected.

In the present specification,

means a portion bonded to another substituent group or a bonding portion.

In the present specification, a halogen group may be fluorine, chlorine, bromine or iodine.

In the present specification, the number of carbon atoms of an imide group is not particularly limited but is preferably 1 to 30. Specifically, the imide group may be compounds having the following structures, but is not limited thereto.

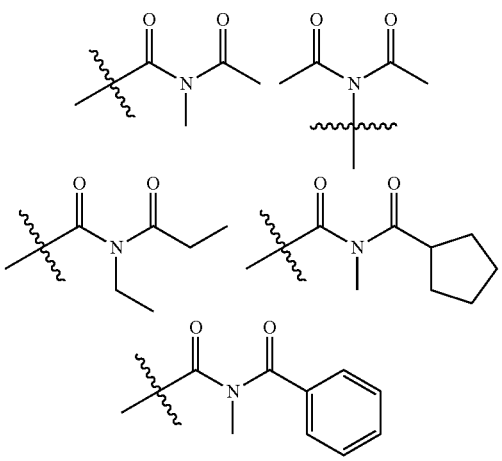

In the present specification, one or two nitrogen atoms of an amide group may be substituted by hydrogen, a straight-chained, branched-chained, or cyclic-chained alkyl group having 1 to 30 carbon atoms, or an aryl group having 6 to 30 carbon atoms. Specifically, the amide group may be compounds having the following Structural Formulas, but is not limited thereto.

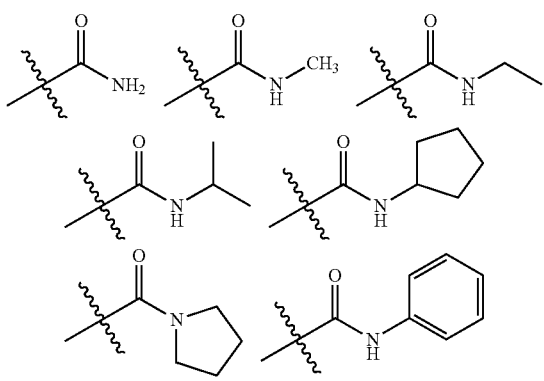

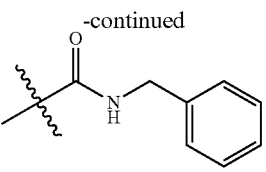

In the present specification, an alkyl group may be a straight or branched chain, and the number of carbon atoms thereof is not particularly limited but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, iso-pentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 30, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be a straight, branched, or cyclic chain. The number of carbon atoms of the alkoxy group is not particularly limited, but preferably 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be a straight or branched chain, and the number of carbon atoms thereof is not particularly limited but is preferably 2 to 30. Specific examples thereof include vinyl, 1-prophenyl, iso-prophenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, an amine group may be selected from the group consisting of —NH$_2$; an alkylamine group; an aralkylamine group; an arylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the case where the aryl group is the monocyclic aryl group, the number of carbon atoms thereof is not particularly limited but is preferably 6 to 25. Specific examples of the monocyclic aryl group may include a phenyl group, a biphenyl group, a terphenyl group, and the like, but are not limited thereto.

In the case where the aryl group is the polycyclic aryl group, the number of carbon atoms thereof is not particularly limited but is preferably 10 to 24. Specific examples of the polycyclic aryl group may include a naphthyl group, a triphenylenyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and the adjacent substituent groups may be bonded to each other to form a cycle.

In the case where the fluorenyl group is substituted,

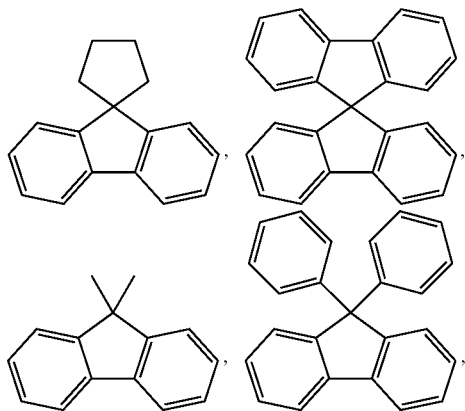

and the like may be formed. However, the fluorenyl group is not limited thereto.

In the present specification, the heterocyclic group includes an atom other than carbon, that is, one or more heteroatoms, and specifically, the heteroatom may include one or more atoms selected from the group consisting of O, N, Se, S, and the like. The number of carbon atoms thereof is not particularly limited, but preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

The heterocyclic group may be a monocycle or a polycycle, and may be aromatics, aliphatics, or a condensation cycle of the aromatics and the aliphatics.

In the present specification, the heteroaryl group may be selected from the aforementioned examples of the heterocyclic group.

In the present specification, the arylene group means a matter where two bonding positions exist at the aryl group, that is, a divalent group. Except that the groups are each the divalent group, the aforementioned description of the aryl group may be applied thereto.

In the present specification, an aromatic cycle may be a monocyclic or a polycycle, and may be selected from the aforementioned examples of the aryl group, except that the aromatic cycle is not monovalent.

In the present specification, the heterocycle may be an aliphatic cycle or an aromatic cycle, means a matter in which at least one carbon atom of the aliphatic or aromatic cycle is substituted by a N, O, or S atom, may be a monocycle or a polycycle, and may be selected from the aforementioned examples of the heteroaryl group, except that the heterocycle is not monovalent.

In the present specification, the "adjacent" group may mean a substituent group substituted in an atom directly connected to an atom where the corresponding substituent group is substituted, a substituent group that is positioned sterically closest to the corresponding substituent group, or another substituent group substituted in an atom where the corresponding substituent group is substituted. For example, two substituent groups substituted at an ortho position in a benzene cycle and two substituent groups substituted at the same carbon in the aliphatic cycle may be interpreted as the groups "adjacent" to each other.

In the present specification, formation of the aromatic cycle by bonding the adjacent groups to each other means formation of a 5-membered to 8-membered monocyclic or polycyclic aromatic cycle by forming a bond between the adjacent substituent groups, and the aromatic cycle may be selected from the aforementioned examples of the aryl group. Specifically, according to the exemplary embodiment of the present specification, the adjacent groups may be bonded to each other to form a fluorene structure.

According to the exemplary embodiment of the present specification, in Chemical Formula 1, at least one of X1 to X3 is N.

In the exemplary embodiment of the present specification, X1 may be N and X2 and X3 may be CH.

In the exemplary embodiment of the present specification, X2 may be N and X1 and X3 may be CH.

In the exemplary embodiment of the present specification, X3 may be N and X1 and X2 may be CH.

According to another exemplary embodiment of the present specification, at least two of X1 to X3 are N.

In the exemplary embodiment of the present specification, X1 and X2 may be N. In this case, X3 is CH.

In the exemplary embodiment of the present specification, X1 and X3 may be N. In this case, X2 is CH.

In the exemplary embodiment of the present specification, X2 and X3 may be N. In this case, X1 is CH.

According to another exemplary embodiment of the present specification, X1 to X3 are N.

According to the exemplary embodiment of the present specification, in Chemical Formula 1, Cy1 and Cy2 are the same as or different from each other, and are each independently a substituted or unsubstituted monocyclic or polycyclic aromatic cycle having 6 to 20 carbon atoms; or a substituted or unsubstituted monocyclic or polycyclic heterocycle having 2 to 20 carbon atoms.

According to another exemplary embodiment of the present specification, Cy1 and Cy2 are the same as or different from each other, and are each independently a substituted or unsubstituted monocyclic or polycyclic aromatic cycle having 6 to 10 carbon atoms; or a substituted or unsubstituted monocyclic or polycyclic heterocycle having 2 to 10 carbon atoms.

According to another exemplary embodiment of the present specification, Cy1 and Cy2 are the same as or different from each other, and are each independently a substituted or unsubstituted benzene cycle; or a substituted or unsubstituted naphthalene cycle.

According to another exemplary embodiment of the present specification, Cy1 and Cy2 are the same as or different from each other, and are each independently a benzene cycle; or a naphthalene cycle.

According to one exemplary embodiment of the present specification, at least one of Cy1 and Cy2 is a substituted or unsubstituted benzene cycle.

According to the exemplary embodiment of the present specification, the compound represented by Chemical Formula 1 is represented by any one of the following Chemical Formulas 1-1 to 1-4.

[Chemical Formula 1-1]

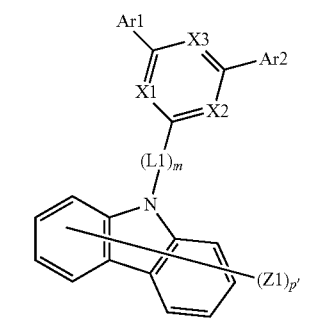

[Chemical Formula 1-2]

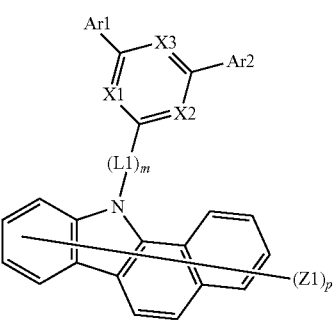

[Chemical Formula 1-3]

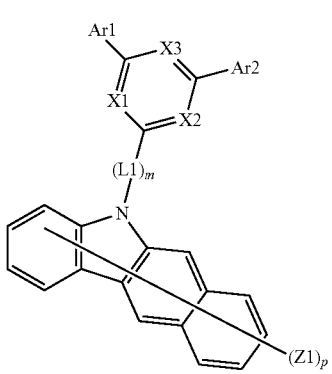

[Chemical Formula 1-4]

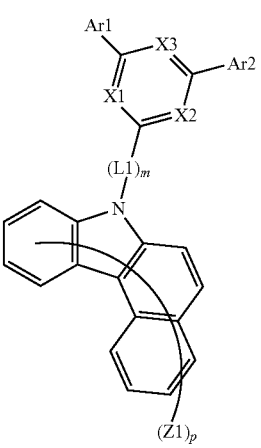

In Chemical Formulas 1-1 to 1-4,
X1 to X3, L1, m, Ar1, and Ar2 are the same as those defined in Chemical Formula 1,
Z1 is deuterium,
p' is an integer of 0 to 8, and
p is an integer of 0 to 10.

According to the exemplary embodiment of the present specification, Chemical Formula 1 is represented by the following Chemical Formula 1-5.

[Chemical Formula 1-5]

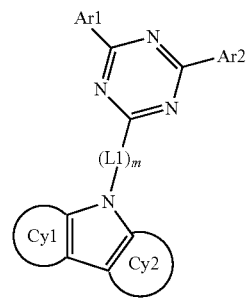

In Chemical Formula 1-5, Cyt, Cy2, L1, m, Ar1, and Ar2 are the same as defined in Chemical Formula 1 according to the aforementioned exemplary embodiment.

According to the exemplary embodiment of the present specification, in Chemical Formula 1, L1 is a substituted or unsubstituted monocyclic or polycyclic arylene group having 6 to 30 carbon atoms.

According to the exemplary embodiment of the present specification, in Chemical Formula 1, L1 is a substituted or unsubstituted monocyclic arylene group having 6 to 30 carbon atoms. In this case, L1 may help an interaction between a structure including Cy1 and Cy2 and a structure including X1 to X3 to help the bipolar type to be stably maintained.

According to another exemplary embodiment of the present specification, L1 is a substituted or unsubstituted monocyclic arylene group having 6 to 24 carbon atoms.

According to another exemplary embodiment of the present specification, L1 is a substituted or unsubstituted phenylene group; or a substituted or unsubstituted biphenylene group.

According to another exemplary embodiment of the present specification, L1 is a substituted or unsubstituted phenylene group; a substituted or unsubstituted biphenylene group; a substituted or unsubstituted terphenylene group; or a substituted or unsubstituted quaterphenylene group.

According to one exemplary embodiment of the present specification, m is 1.

According to another exemplary embodiment, m is 2.

According to another exemplary embodiment, m is 3.

According to another exemplary embodiment, m is 4.

According to another exemplary embodiment of the present specification, L1 is a phenylene group; a biphenylene group; a terphenylene group; or a quaterphenylene group.

According to another exemplary embodiment of the present specification, L1 is a phenylene group; or a biphenylene group, and m is 1 or 2, and in the case where m is 2, L1s are the same as or different from each other.

In one exemplary embodiment of the present specification, $(L1)_m$ is represented by the following Chemical Formula 3.

[Chemical Formula 3]

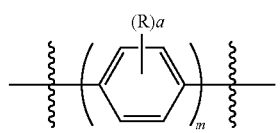

In Chemical Formula 3,

R is a substituent group, a is an integer of 1 to 4, in the case where a is an integer of 2 to 4, 2 to 4 Rs are the same as or different from each other, m is an integer of 1 to 4, and in the case where m is an integer of 2 to 4, 2 to 4 structures in brackets are the same as or different from each other.

The substituent group R may be selected from the aforementioned examples of the substituent group.

According to the exemplary embodiment of the present specification, in the case where $(L1)_m$ is Chemical Formula 3, a cycle including Cy1 and Cy2 and a cycle including X1 to X3 may be connected in a linear form to structurally connect the p type and the n type and thus increase an interaction thereof, thereby stably serving as the bipolar type.

According to the exemplary embodiment of the present specification, the compound represented by Chemical Formula 1 is represented by any one of the following Chemical Formulas 1-6 to 1-9.

[Chemical Formula 1-6]

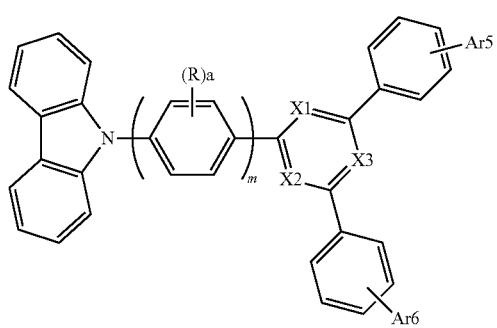

[Chemical Formula 1-7]

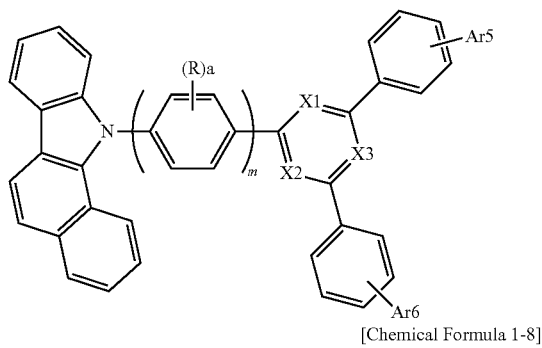

[Chemical Formula 1-8]

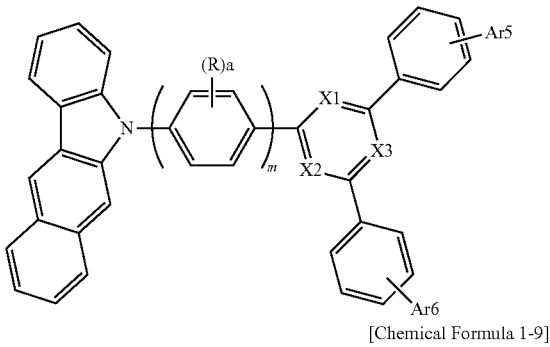

[Chemical Formula 1-9]

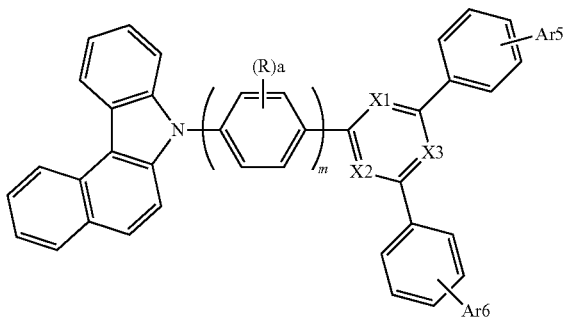

In Chemical Formulas 1-6 to 1-9,

X1 to X3 are the same as or different from each other, and are each independently N or CH, at least one of X1 to X3 is N, Ar5 and Ar6 are the same as or different from each other, and are each independently hydrogen; deuterium; a substituted or unsubstituted alkyl group having 1 to 20 carbon atoms; a substituted or unsubstituted monocyclic or polycyclic aryl group having 6 to 30 carbon atoms; or a substituted or unsubstituted monocyclic or polycyclic heteroaryl group having 2 to 30 carbon atoms, or are bonded to a phenyl group to form a cycle, R is a substituent group, a is an integer of 1 to 4, in the case where a is an integer of 2 to 4, 2 to 4 Rs are the same as or different from each other, m is an integer of 1 to 4, and in the case where m is an integer of 2 to 4, 2 to 4 structures in brackets are the same as or different from each other.

According to another exemplary embodiment of the present specification, Ar5 and Ar6 are the same as or different from each other, and are each independently hydrogen; deuterium; a substituted or unsubstituted alkyl group having 1 to 10 carbon atoms; a substituted or unsubstituted monocyclic or polycyclic aryl group having 6 to 20 carbon atoms; or a substituted or unsubstituted monocyclic or polycyclic heteroaryl group having 2 to 20 carbon atoms, or are bonded to a phenyl group to form a cycle.

According to another exemplary embodiment of the present specification, Ar5 and Ar6 are the same as or different from each other, and are each independently hydrogen; deuterium; a substituted or unsubstituted alkyl group having 1 to 5 carbon atoms; a substituted or unsubstituted monocyclic or polycyclic aryl group having 6 to 10 carbon atoms; or a substituted or unsubstituted monocyclic or polycyclic heteroaryl group having 2 to 10 carbon atoms, or are bonded to a phenyl group to form a cycle.

Formation of the cycle by bonding to the phenyl group means formation of a condensation cycle by bonding the phenyl group and Ar5 or Ar6, and in this case, the structure including X1 to X3 may be substituted by a polycycle. In the present specification, the cycle may be an aliphatic hydrocarbon cycle, an aromatic hydrocarbon cycle, an aliphatic heterocycle, an aromatic heterocycle, or the like.

According to another exemplary embodiment of the present specification, Ar5 and Ar6 are the same as or different from each other, and are each independently hydrogen; a substituted or unsubstituted methyl group; a substituted or unsubstituted phenyl group; a substituted or unsubstituted biphenyl group; or a substituted or unsubstituted naphthyl group, or are bonded to a phenyl group to form a substituted or unsubstituted naphthalene cycle, a substituted or unsubstituted triphenylene cycle, a substituted or unsubstituted fluorene cycle; or a substituted or unsubstituted phenanthrene cycle.

According to another exemplary embodiment of the present specification, Ar5 and Ar6 are the same as or different from each other, and are each independently a methyl group; a triphenylmethyl group; a phenyl group; a naphthyl group; or a biphenyl group, or are bonded to a phenyl group to form a naphthalene cycle; a triphenylene cycle; a fluorene cycle substituted by a phenyl group; or a phenanthrene cycle.

According to the exemplary embodiment of the present specification, in Chemical Formula 1, Ar1 and Ar2 are the same as or different from each other, and are each independently selected from the group consisting of a substituted or unsubstituted monocyclic or polycyclic aryl group having 6 to 20 carbon atoms; and a substituted or unsubstituted monocyclic or polycyclic heteroaryl group having 2 to 20 carbon atoms.

According to another exemplary embodiment of the present specification, Ar1 and Ar2 are the same as or different from each other, and are each independently a substituted or unsubstituted phenyl group; a substituted or unsubstituted biphenyl group; a substituted or unsubstituted terphenyl group; a substituted or unsubstituted naphthyl group; a substituted or unsubstituted triphenylenyl group; a substituted or unsubstituted fluorenyl group; or a substituted or unsubstituted phenanthrenyl group.

According to another exemplary embodiment of the present specification, Ar1 and Ar2 are the same as or different from each other, and are each independently a phenyl group; a biphenyl group; a terphenyl group; a naphthyl group; a triphenylenyl group; a fluorenyl group; or a phenanthrenyl group, and the phenyl group, the biphenyl group, the terphenyl group, the naphthyl group, the triphenylenyl group, the fluorenyl group, and the threnyl group are unsubstituted or substituted by one or two or more substituent groups selected from the group consisting of a substituted or unsubstituted alkyl group and a substituted or unsubstituted aryl group.

According to another exemplary embodiment of the present specification, Ar1 and Ar2 are the same as or different from each other, and are each independently selected from the group consisting of a phenyl group; a phenyl group substituted by a methyl group; a phenyl group substituted by a triphenylmethyl group; a phenyl group substituted by a naphthyl group; a phenyl group substituted by a phenyl group; a phenyl group substituted by a terphenyl group; a biphenyl group; a biphenyl group substituted by a phenyl group; a naphthyl group; a triphenylenyl group; a fluorenyl group substituted by a phenyl group; and a phenanthrenyl group.

According to the exemplary embodiment of the present specification, Ar1 and Ar2 are the same as or different from each other, and are each independently any one of the following substituent groups.

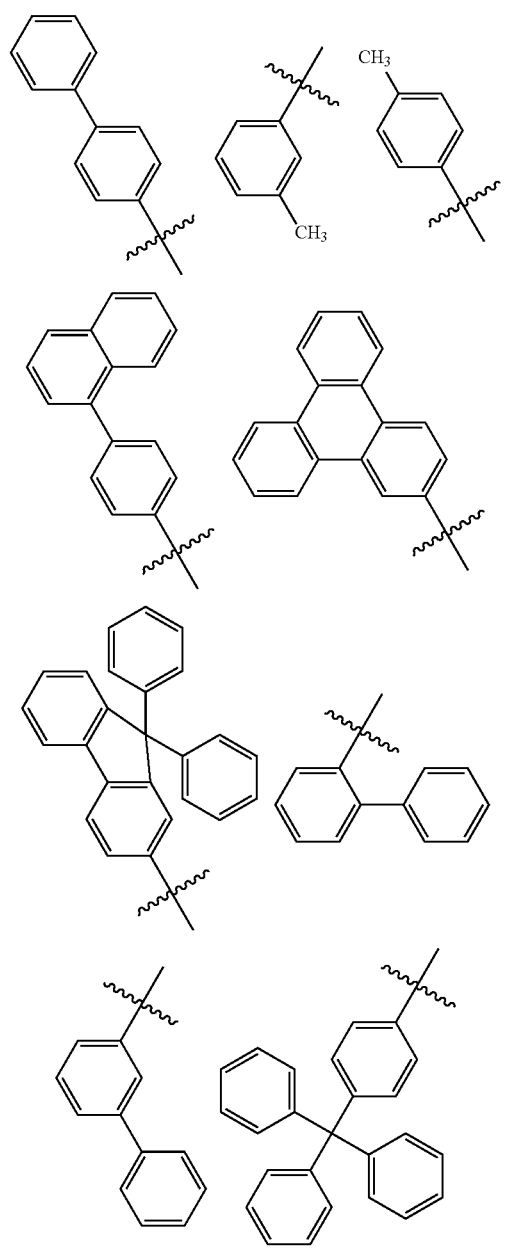

-continued

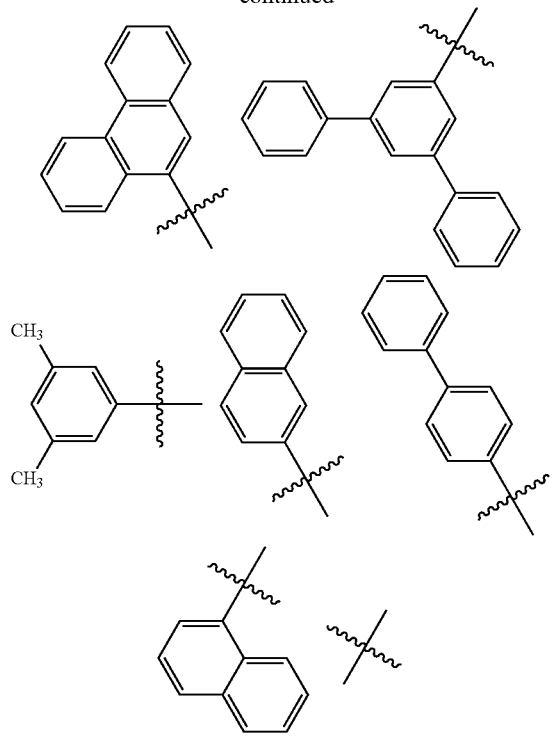

is a portion connected to the cycle including X1 to X3 of Chemical Formula 1.

According to the exemplary embodiment of the present specification, p' is 0.

According to one exemplary embodiment, p is 0.

According to the exemplary embodiment of the present specification, the compound represented by Chemical Formula 1 is represented by any one of the following compounds.

According to one exemplary embodiment, the compound represented by Chemical Formula 1-1 is represented by any one of the following Chemical Formulas 1-1-1 to 1-1-37.

According to another exemplary embodiment, the compound represented by Chemical Formula 1-2 is represented by any one of the following Chemical Formulas 1-2-1 to 1-2-8.

According to another exemplary embodiment, the compound represented by Chemical Formula 1-3 is represented by any one of the following Chemical Formulas 1-3-1 to 1-3-8.

According to another exemplary embodiment, the compound represented by Chemical Formula 1-4 is represented by any one of the following Chemical Formulas 1-4-1 to 1-4-8.

Chemical Formula 1-1-1

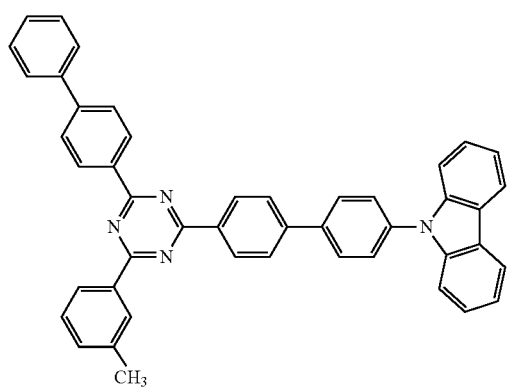

Chemical Formula 1-1-2

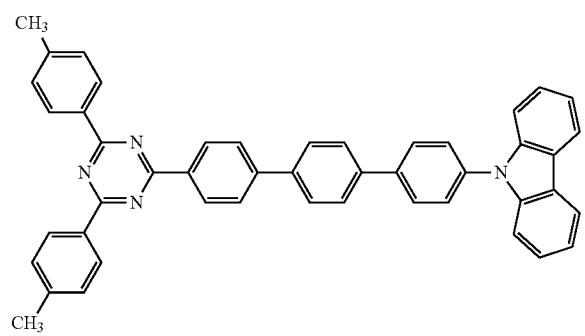

Chemical Formula 1-1-3

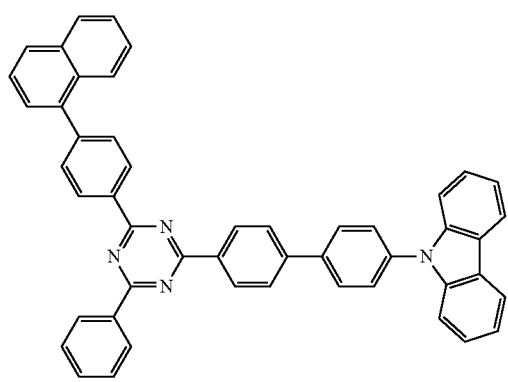

Chemical Formula 1-1-4

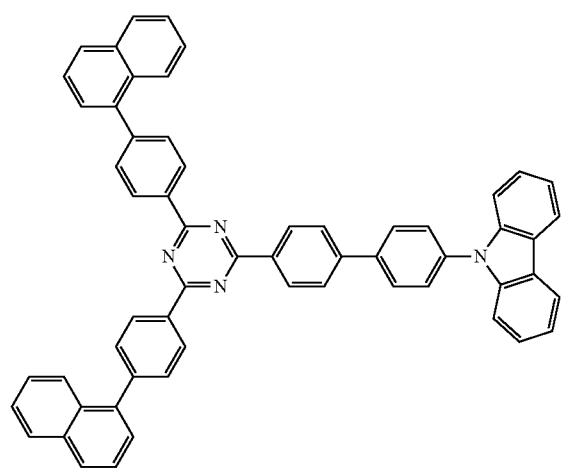

Chemical Formula 1-1-5
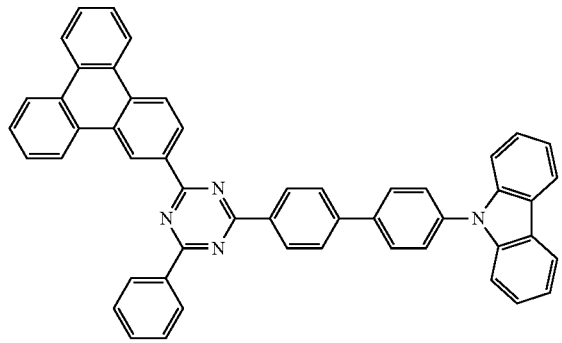
Chemical Formula 1-1-6
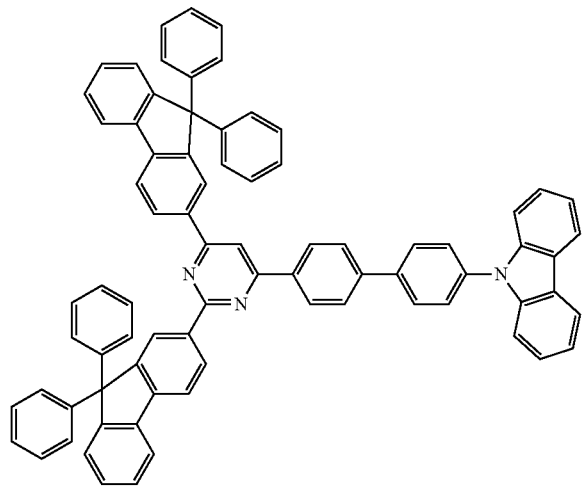
Chemical Formula 1-1-7
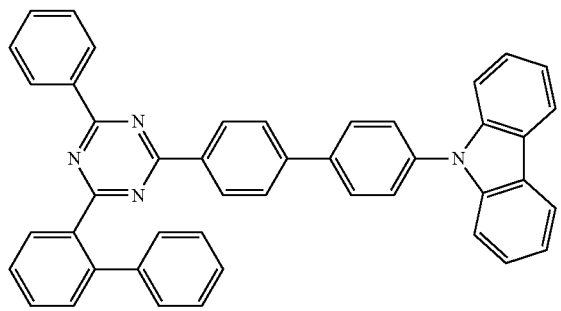
Chemical Formula 1-1-8
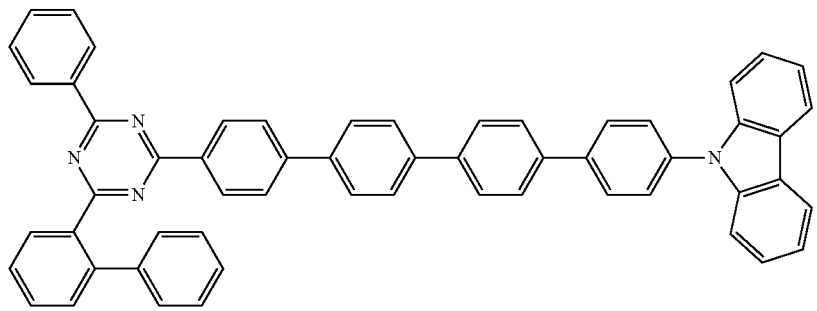
Chemical Formula 1-1-9
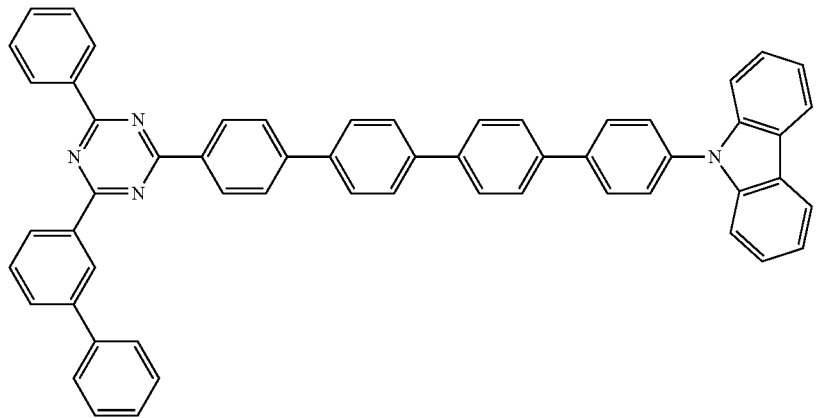

-continued
Chemical Formula 1-1-10
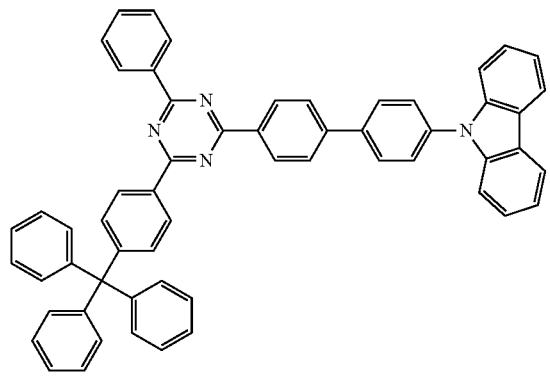
Chemical Formula 1-1-11
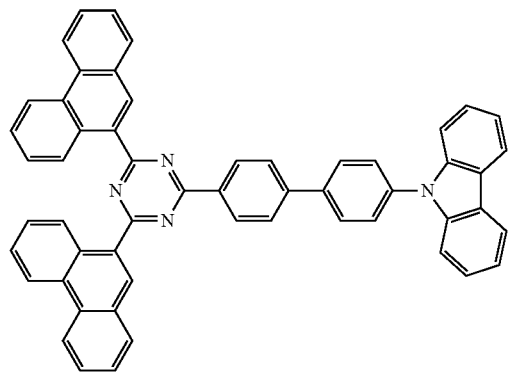
Chemical Formula 1-1-12
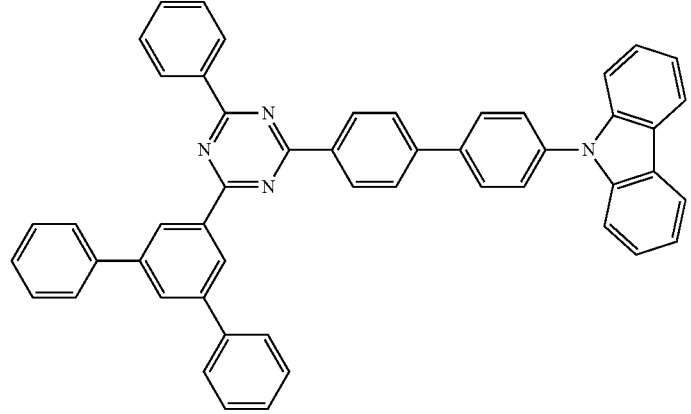
Chemical Formula 1-1-13
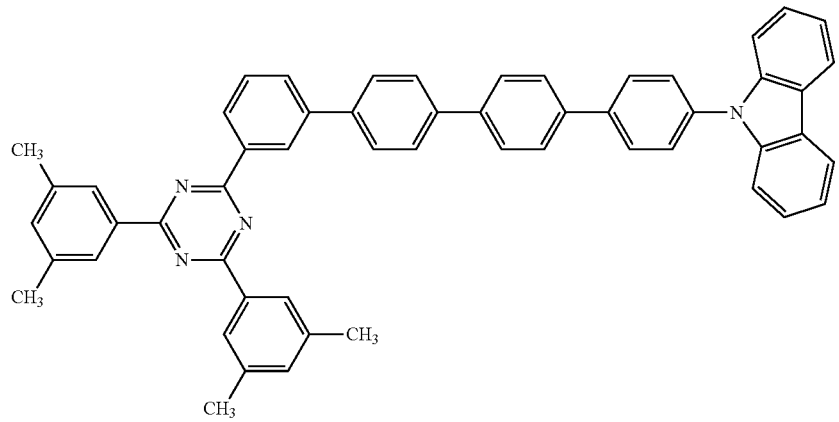
Chemical Formula 1-1-14
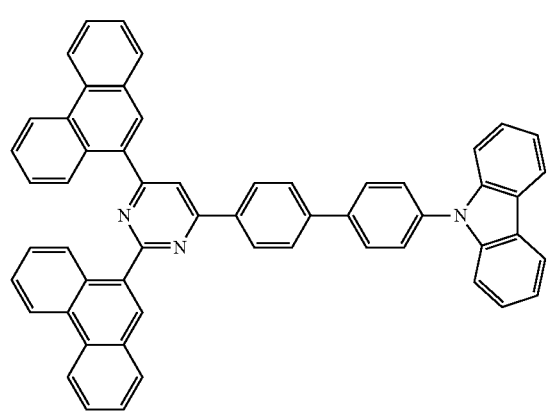
Chemical Formula 1-1-15
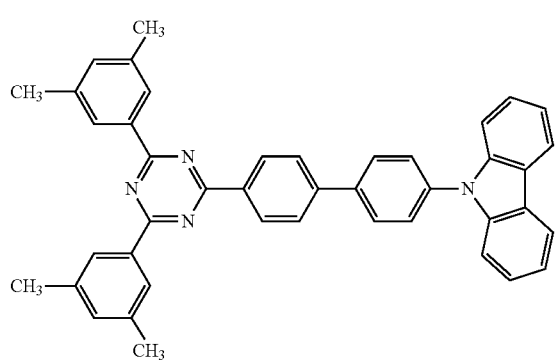

Chemical Formula 1-1-16
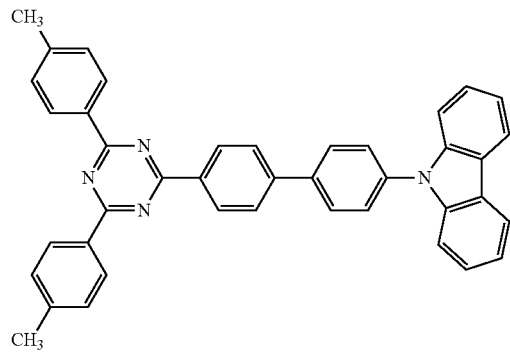
Chemical Formula 1-1-17
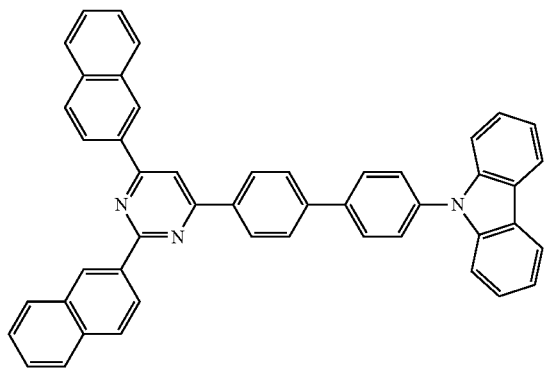
Chemical Formula 1-1-18
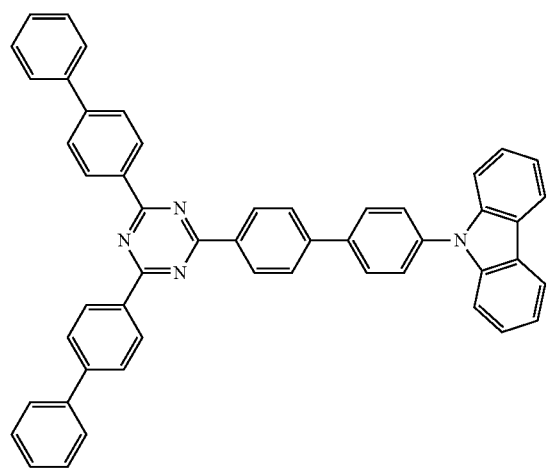
Chemical Formula 1-1-19
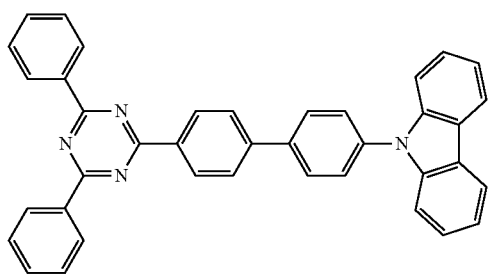
Chemical Formula 1-1-20
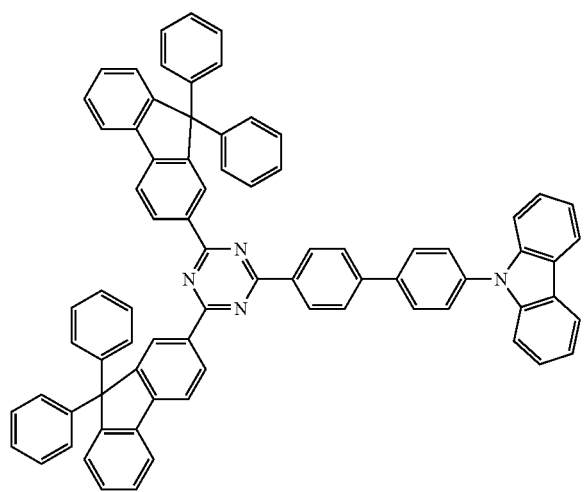
Chemical Formula 1-1-21
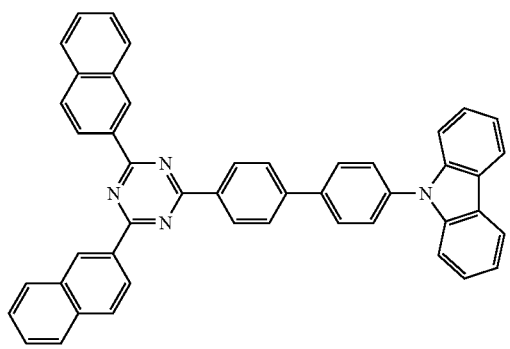

-continued
Chemical Formula 1-1-22
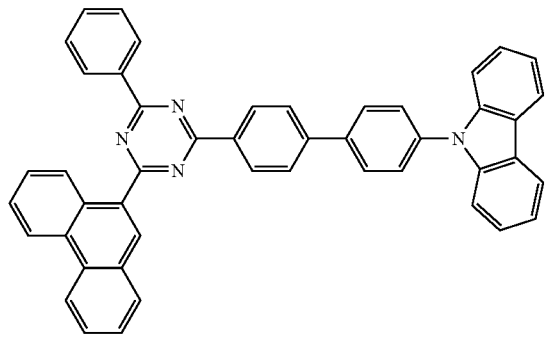
Chemical Formula 1-1-23
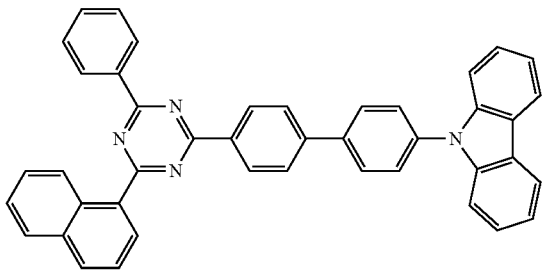
Chemical Formula 1-1-24
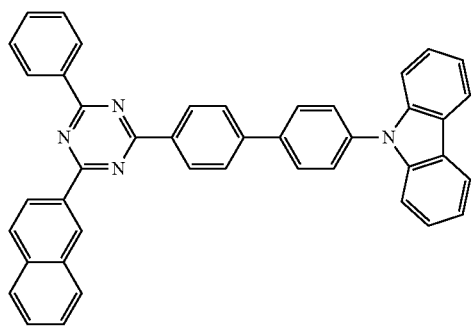
Chemical Formula 1-1-25
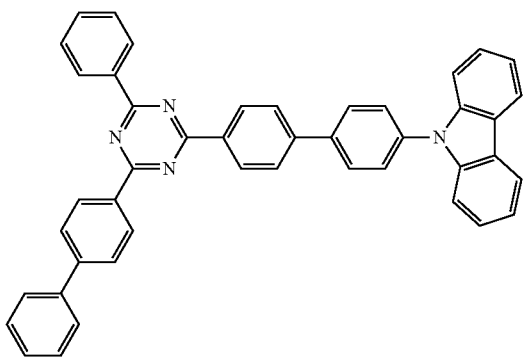
Chemical Formula 1-1-26
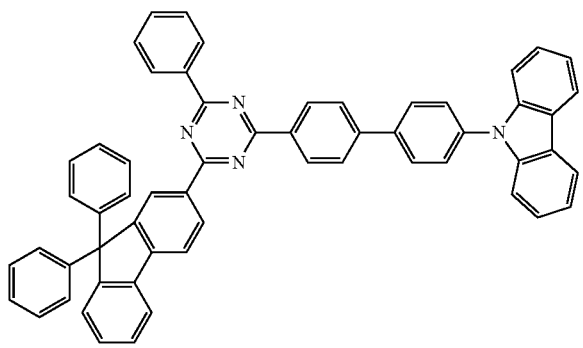
Chemical Formula 1-1-27
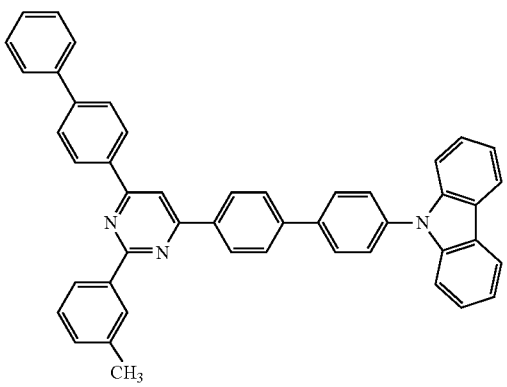
Chemical Formula 1-1-28
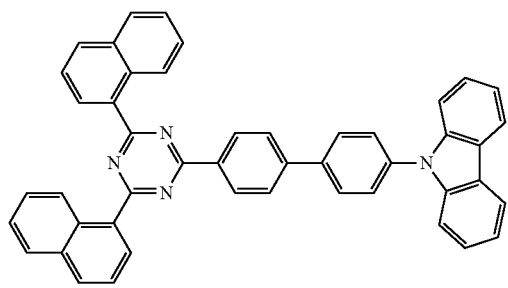
Chemical Formula 1-1-29
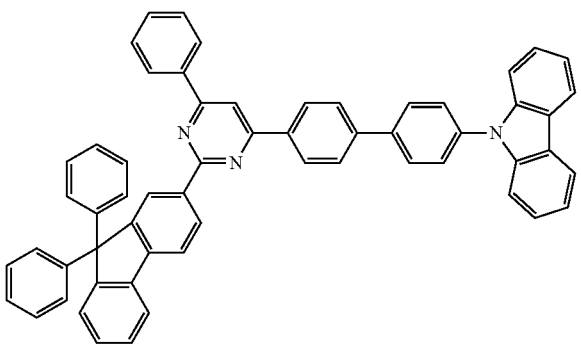

Chemical Formula 1-1-30
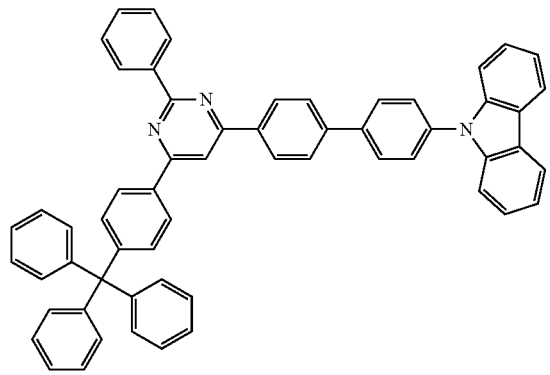
Chemical Formula 1-1-31
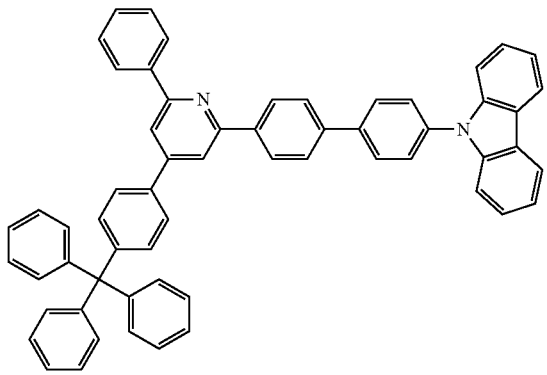
Chemical Formula 1-1-32
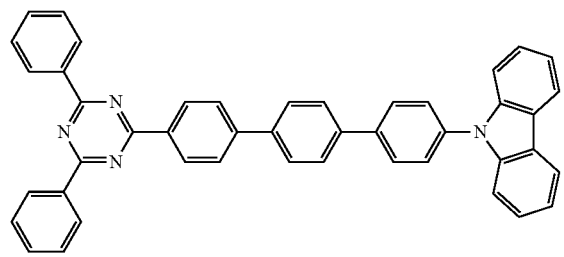
Chemical Formula 1-1-33
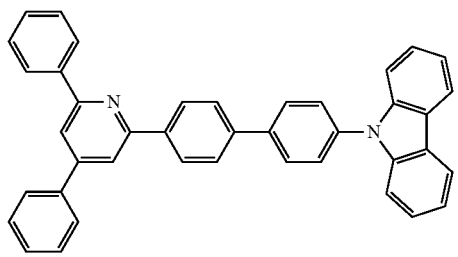
Chemical Formula 1-1-34
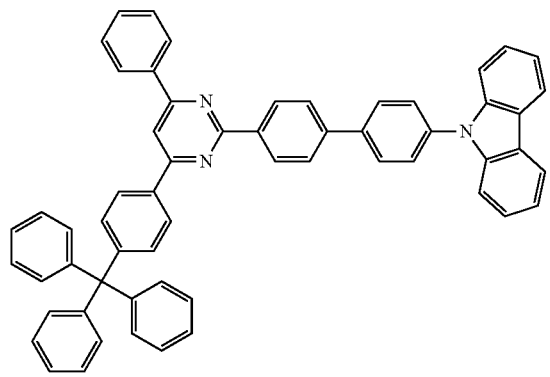
Chemical Formula 1-1-35
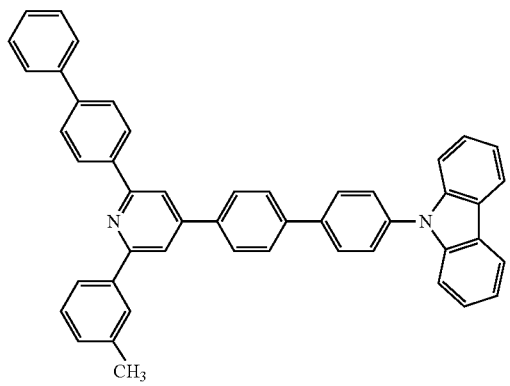
Chemical Formula 1-1-36
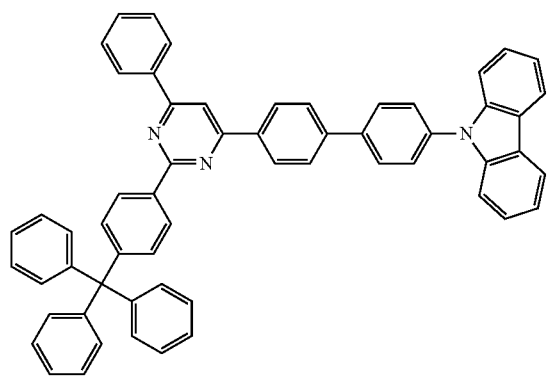
Chemical Formula 1-1-37
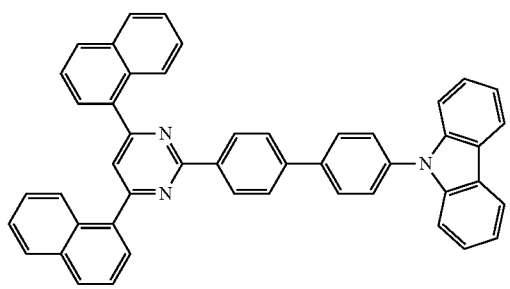

-continued
Chemical Formula 1-2-1
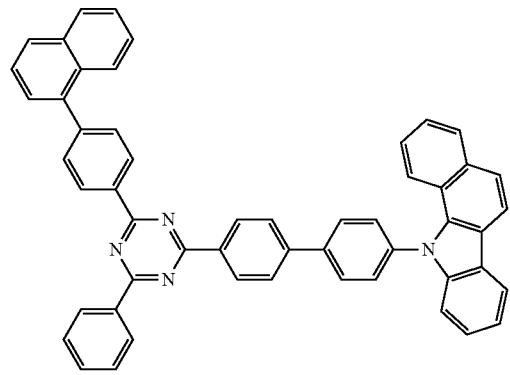
Chemical Formula 1-2-2
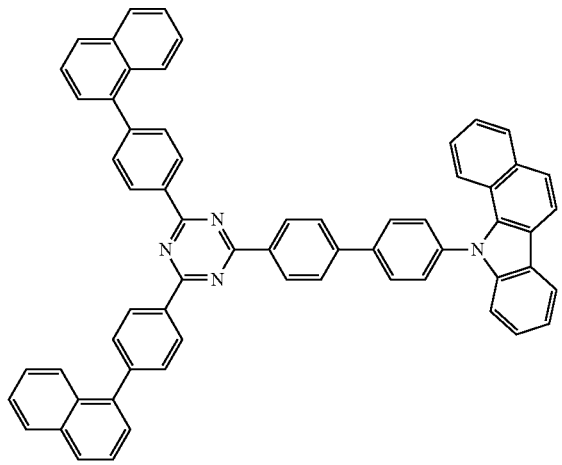
Chemical Formula 1-2-3
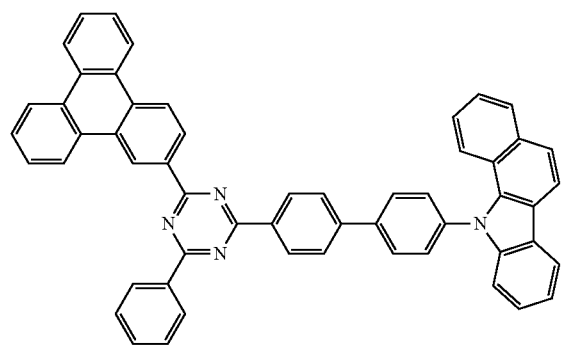
Chemical Formula 1-2-4
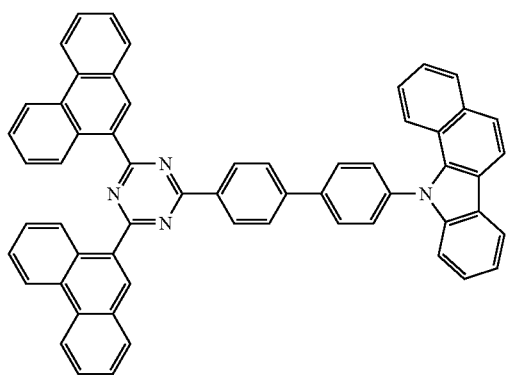
Chemical Formula 1-2-5
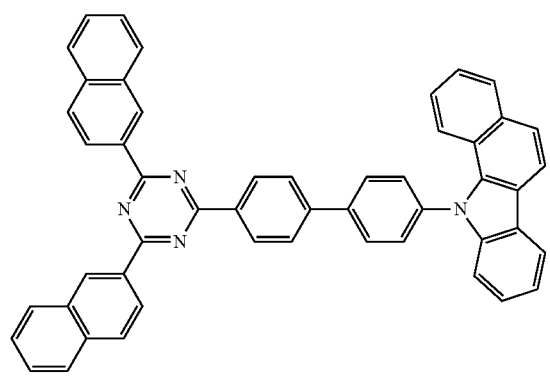
Chemical Formula 1-2-6
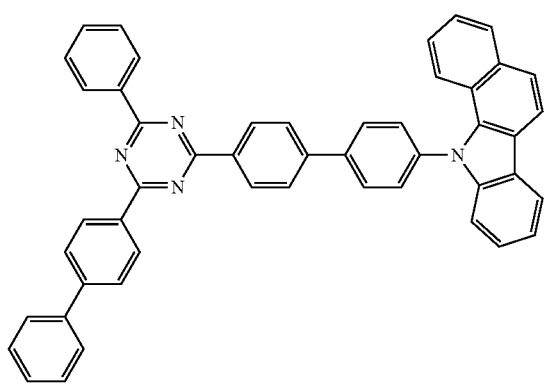

-continued
Chemical Formula 1-2-7
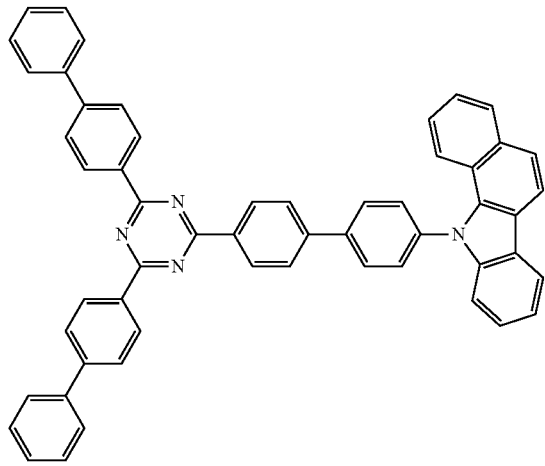
Chemical Formula 1-2-8
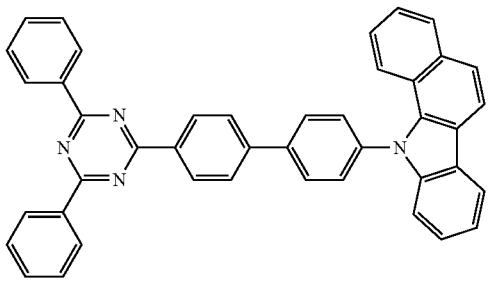
Chemical Formula 1-3-1
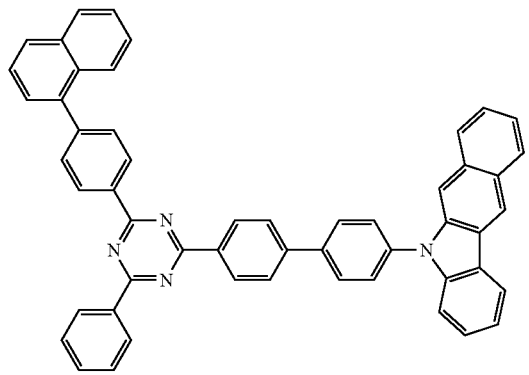
Chemical Formula 1-3-2
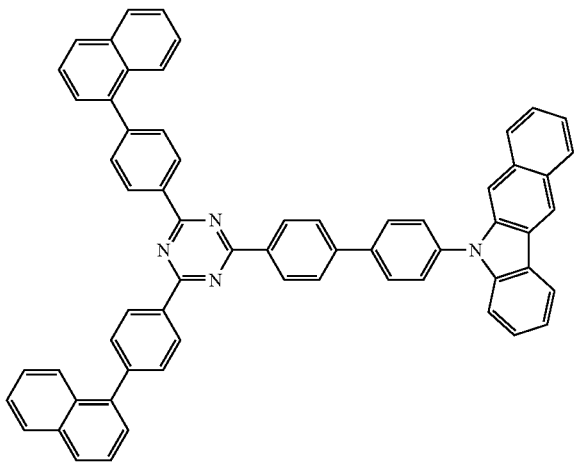
Chemical Formula 1-3-3
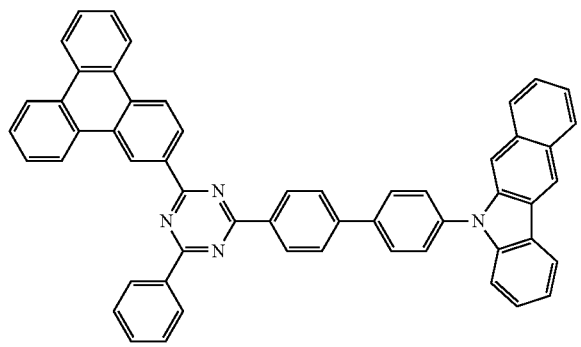
Chemical Formula 1-3-4
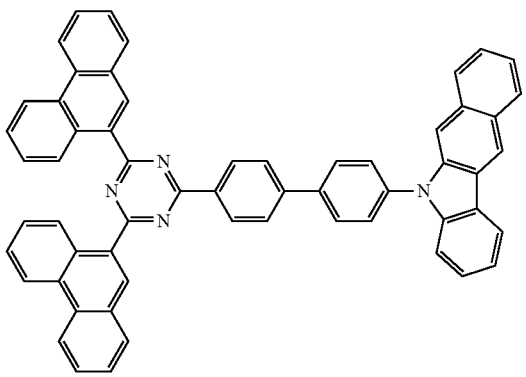

Chemical Formula 1-3-5
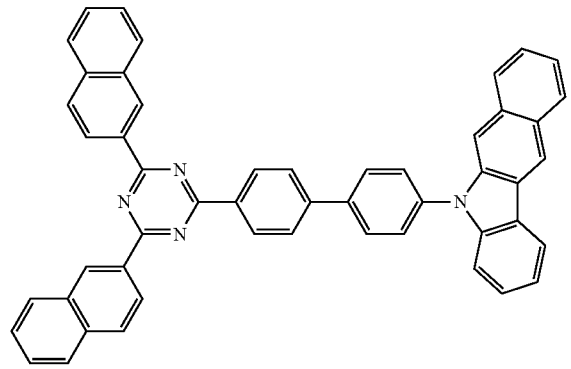
Chemical Formula 1-3-6
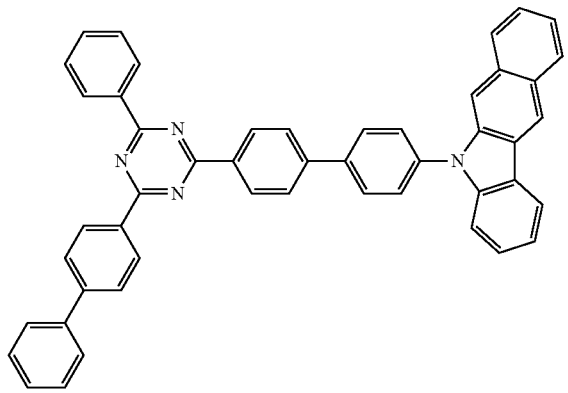
Chemical Formula 1-3-7
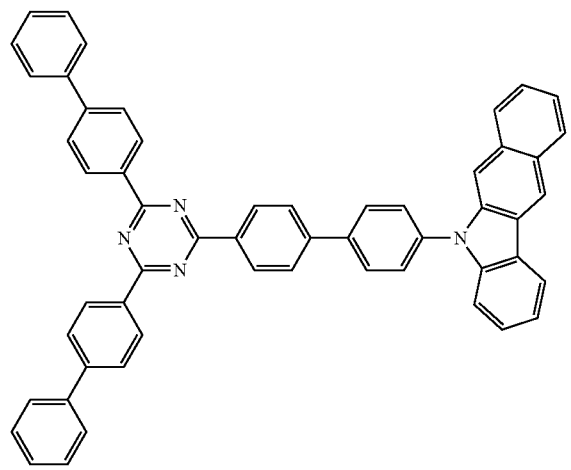
Chemical Formula 1-3-8
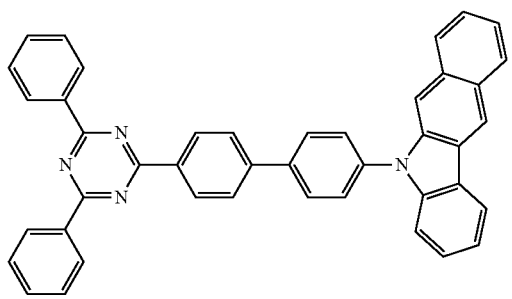
Chemical Formula 1-4-1
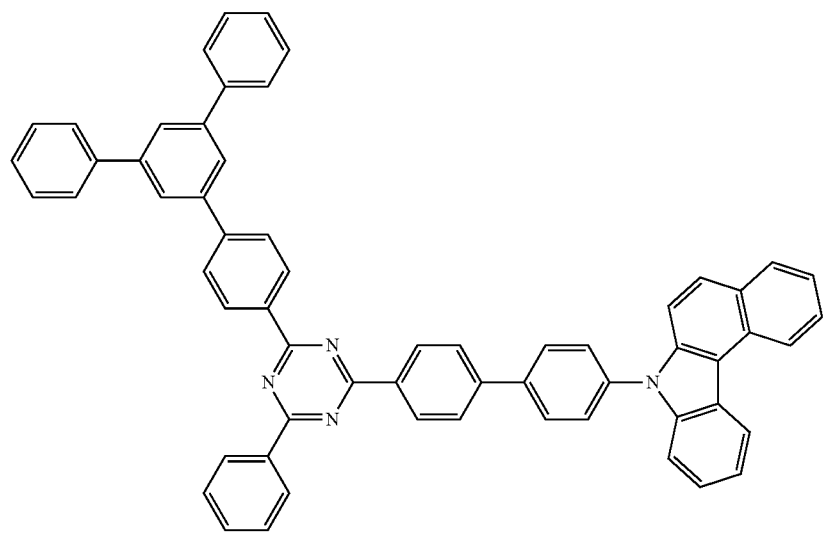

-continued
Chemical Formula 1-4-2
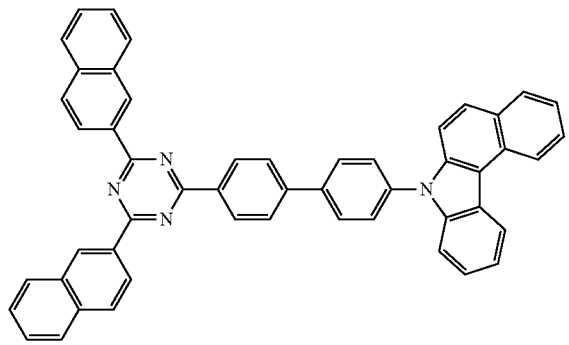
Chemical Formula 1-4-3
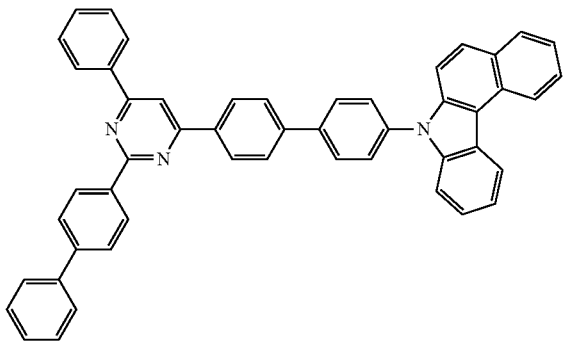
Chemical Formula 1-4-4
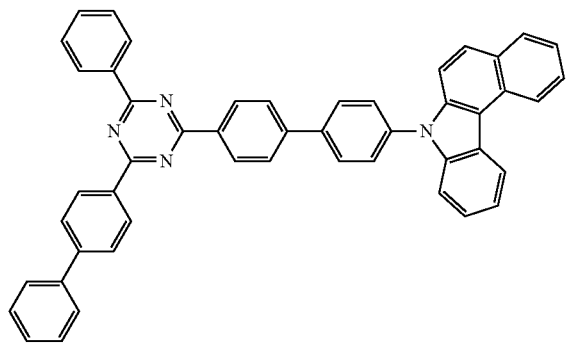
Chemical Formula 1-4-5
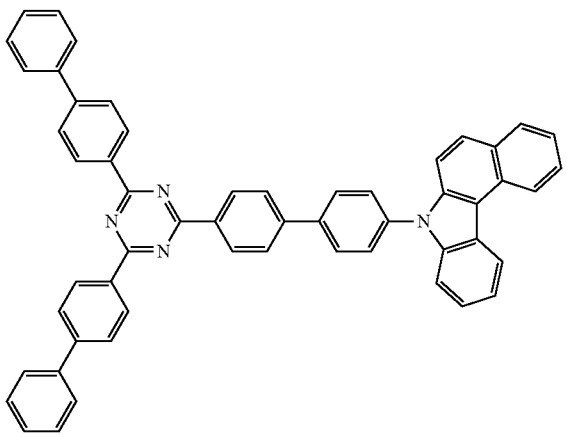
Chemical Formula 1-4-6
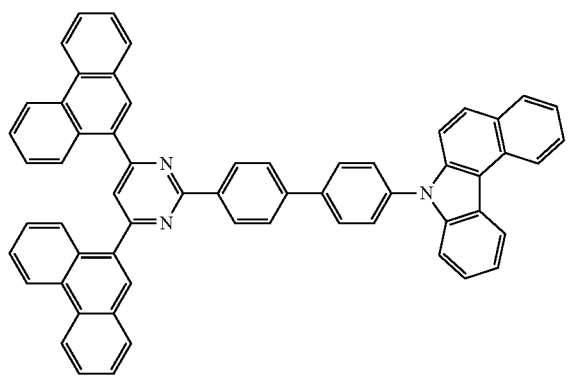
Chemical Formula 1-4-7
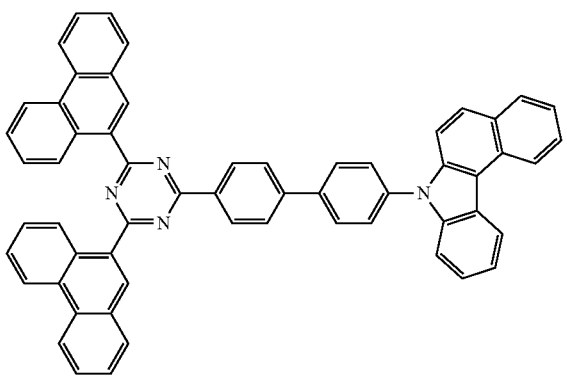
Chemical Formula 1-4-8
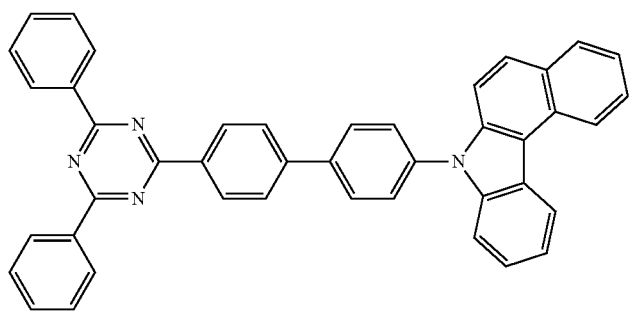

According to the exemplary embodiment of the present specification, in Chemical Formula 2, Ar3 and Ar4 are the same as or different from each other, and are a substituted or unsubstituted monocyclic or polycyclic aryl group having 6 to 20 carbon atoms; or a substituted or unsubstituted monocyclic or polycyclic heteroaryl group having 2 to 20 carbon atoms.

According to another exemplary embodiment of the present specification, Ar3 and Ar4 are the same as or different from each other, and are a substituted or unsubstituted monocyclic or polycyclic aryl group having 6 to 15 carbon atoms; or a substituted or unsubstituted monocyclic or polycyclic heteroaryl group having 2 to 15 carbon atoms.

According to another exemplary embodiment of the present specification, Ar3 and Ar4 are the same as or different from each other, and are a substituted or unsubstituted phenyl group; a substituted or unsubstituted biphenyl group; or a substituted or unsubstituted fluorenyl group.

According to another exemplary embodiment of the present specification, Ar3 and Ar4 are the same as or different from each other, and are a phenyl group; a phenyl group substituted by a phenyl group; a phenyl group substituted by a pyridine group; a biphenyl group; or a fluorenyl group substituted by a methyl group.

According to the exemplary embodiment of the present specification, Ar3 is a substituted or unsubstituted phenyl group; a substituted or unsubstituted biphenyl group; or a substituted or unsubstituted fluorenyl group.

In one exemplary embodiment of the present specification, Ar3 is a substituted or unsubstituted phenyl group.

In another exemplary embodiment, Ar3 is a phenyl group substituted by an aryl group.

In the exemplary embodiment of the present specification, Ar3 is a phenyl group substituted by a phenyl group.

In another exemplary embodiment, Ar3 is a phenyl group.

In the exemplary embodiment of the present specification, Ar3 is a phenyl group substituted by a heterocyclic group.

In another exemplary embodiment, Ar3 is a phenyl group substituted by a nitrogen-containing heterocyclic group.

In another exemplary embodiment, Ar3 is a phenyl group substituted by a pyridine group.

In the exemplary embodiment of the present specification, a phenyl group substituted by the pyridine group is

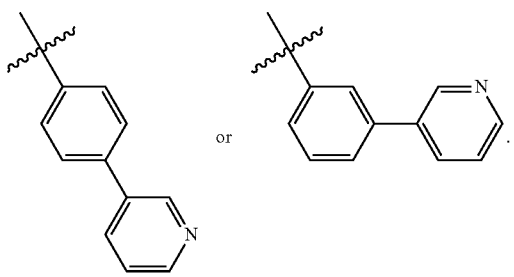 [SMILES: *c1ccc(-c2cccnc2)cc1 ; *c1cccc(-c2cccnc2)c1]

In another exemplary embodiment, Ar3 is a substituted or unsubstituted biphenyl group.

In another exemplary embodiment, Ar3 is a phenyl group.

In the exemplary embodiment of the present specification, the biphenyl group is

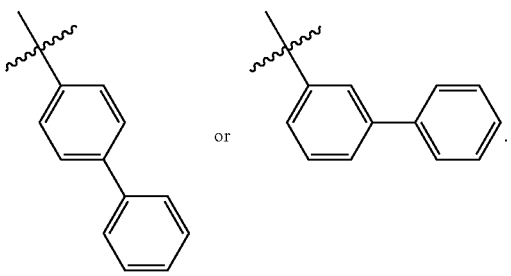 [SMILES: *c1ccc(-c2ccccc2)cc1 ; *c1cccc(-c2ccccc2)c1]

In the exemplary embodiment of the present specification, Ar3 is a substituted or unsubstituted fluorenyl group.

In another exemplary embodiment, Ar3 is a fluorenyl group substituted by an alkyl group.

In the exemplary embodiment of the present specification, Ar3 is a fluorenyl group substituted by a methyl group.

According to one exemplary embodiment of the present specification, Ar4 is a substituted or unsubstituted phenyl group; or a substituted or unsubstituted biphenyl group.

In one exemplary embodiment, Ar4 is a substituted or unsubstituted phenyl group.

In another exemplary embodiment, Ar4 is a phenyl group.

In another exemplary embodiment, Ar4 is a substituted or unsubstituted biphenyl group.

In another exemplary embodiment, Ar4 is a biphenyl group.

According to the exemplary embodiment of the present specification, in Chemical Formula 2, L2 is a substituted or unsubstituted monocyclic or polycyclic arylene group having 6 to 20 carbon atoms.

According to another exemplary embodiment of the present specification, L2 is a substituted or unsubstituted monocyclic or polycyclic arylene group having 6 to 10 carbon atoms.

According to another exemplary embodiment of the present specification, L2 is a substituted or unsubstituted phenylene group; a substituted or unsubstituted biphenylene group; or a substituted or unsubstituted naphthalene group, or n is 0.

According to the exemplary embodiment of the present specification, $(L2)_n$ is a direct bond; a substituted or unsubstituted phenylene group; a substituted or unsubstituted biphenylene group; or a substituted or unsubstituted naphthalene group.

According to the exemplary embodiment of the present specification, $(L2)_n$ is a direct bond; a phenylene group; a biphenylene group; or a naphthalene group.

According to the exemplary embodiment of the present specification, in Chemical Formula 2, R1 to R7 are the same as or different from each other, and are each independently selected from the group consisting of hydrogen; deuterium; a substituted or unsubstituted straight-chained or branch-chained alkyl group having 1 to 20 carbon atoms; a substituted or unsubstituted monocyclic or polycyclic aryl group having 6 to 20 carbon atoms; and a substituted or unsubstituted monocyclic or polycyclic heteroaryl group having 2 to 20 carbon atoms.

According to another exemplary embodiment of the present specification, R1 to R7 are the same as or different from each other, and are each independently selected from the group consisting of hydrogen; deuterium; a substituted or unsubstituted straight-chained or branch-chained alkyl group having 1 to 10 carbon atoms; a substituted or unsubstituted monocyclic or polycyclic aryl group having 6 to 10 carbon atoms; and a substituted or unsubstituted monocyclic or polycyclic heteroaryl group having 2 to 10 carbon atoms.

According to one exemplary embodiment of the present specification, R1 to R7 are the same as or different from each other, and are each independently hydrogen; or a substituted or unsubstituted monocyclic or polycyclic aryl group having 6 to 30 carbon atoms.

According to another exemplary embodiment, R1 to R7 are the same as or different from each other, and are each independently hydrogen; or a substituted or unsubstituted phenyl group.

In the exemplary embodiment of the present specification, R1 is hydrogen.

In another exemplary embodiment, R2 is hydrogen.

In the exemplary embodiment of the present specification, R3 is hydrogen.

In the exemplary embodiment of the present specification, R4 is hydrogen.

In the exemplary embodiment of the present specification, R5 is hydrogen.

In another exemplary embodiment, R5 is a substituted or unsubstituted monocyclic or polycyclic aryl group having 6 to 30 carbon atoms.

In another exemplary embodiment, R5 is a substituted or unsubstituted phenyl group.

In another exemplary embodiment, R5 is a phenyl group.

In the exemplary embodiment of the present specification, R6 is hydrogen.

In another exemplary embodiment, R7 is hydrogen.

According to the exemplary embodiment of the present specification, in Chemical Formula 2, Y1 and Y2 are the same as or different from each other, and are each independently a substituted or unsubstituted straight-chained or branch-chained alkyl group having 1 to 20 carbon atoms; a substituted or unsubstituted monocyclic or polycyclic aryl group having 6 to 20 carbon atoms; or a substituted or unsubstituted monocyclic or polycyclic heteroaryl group having 2 to 20 carbon atoms, or Y1 and Y2 are bonded to each other to form a substituted or unsubstituted aromatic cycle.

According to another exemplary embodiment of the present specification, Y1 and Y2 are the same as or different from each other, and are each independently a substituted or unsubstituted straight-chained or branch-chained alkyl group having 1 to 15 carbon atoms; a substituted or unsubstituted monocyclic or polycyclic aryl group having 6 to 15 carbon atoms; or a substituted or unsubstituted monocyclic or polycyclic heteroaryl group having 2 to 15 carbon atoms, or Y1 and Y2 are bonded to each other to form a substituted or unsubstituted aromatic cycle.

According to another exemplary embodiment of the present specification, Y1 and Y2 are the same as or different from each other, and are each independently a substituted or unsubstituted alkyl group having 1 to 10 carbon atoms; or a substituted or unsubstituted phenyl group, or are bonded to each other to form a substituted or unsubstituted fluorene structure.

According to another exemplary embodiment of the present specification, Y1 and Y2 are the same as or different from each other, and are each independently a methyl group; or a phenyl group, or are bonded to each other to form a fluorene structure.

According to one exemplary embodiment of the present specification, in the case where Y1 and Y2 are bonded to each other to form the fluorene structure, the fluorenyl group including Y1 and Y2 of Chemical Formula 2 may have a spirobifluorene structure.

According to the exemplary embodiment of the present specification, the compound represented by Chemical Formula 2 is represented by any one of the following Chemical Formulas 2-1 to 2-22.

Chemical Formula 2-1

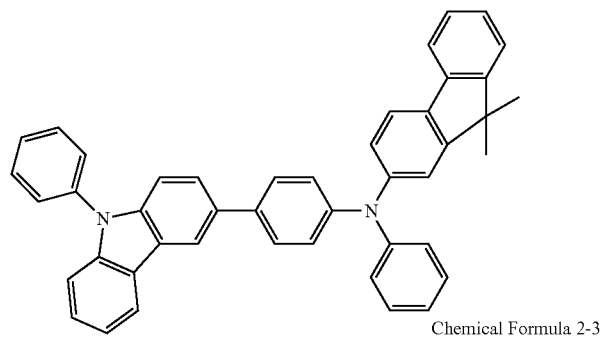

Chemical Formula 2-2

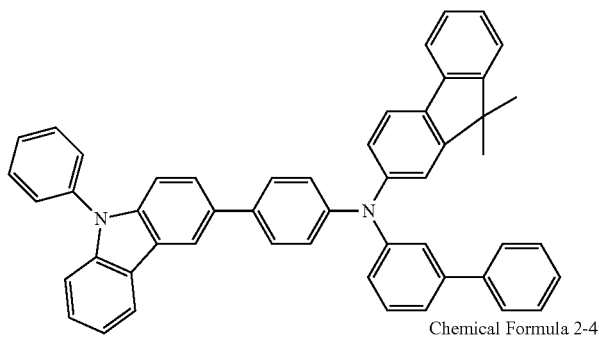

Chemical Formula 2-3

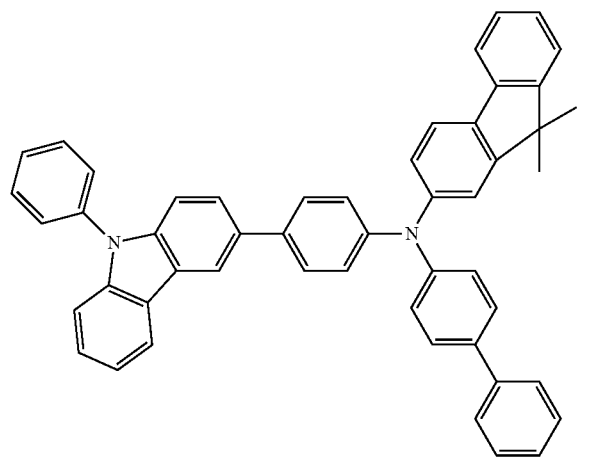

Chemical Formula 2-4

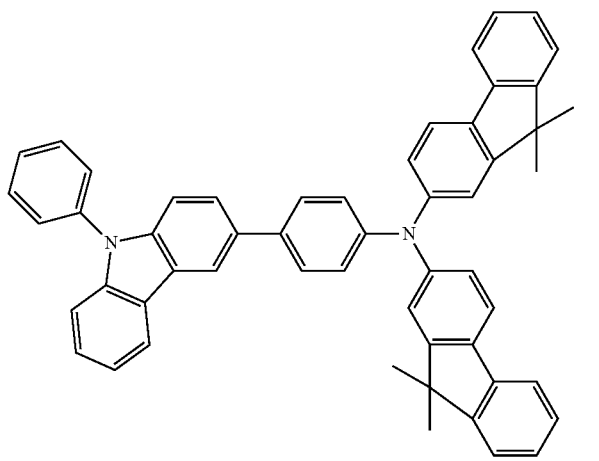

-continued
Chemical Formula 2-5
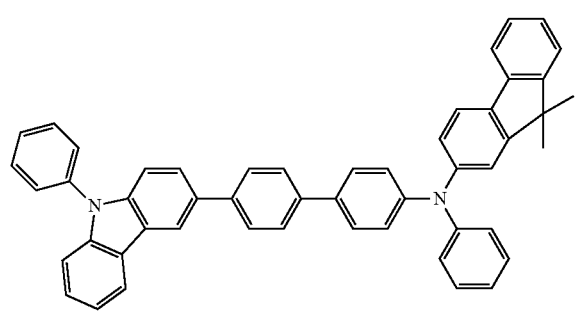
Chemical Formula 2-6
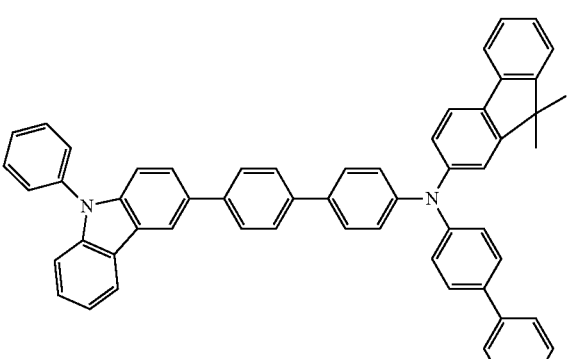
Chemical Formula 2-7
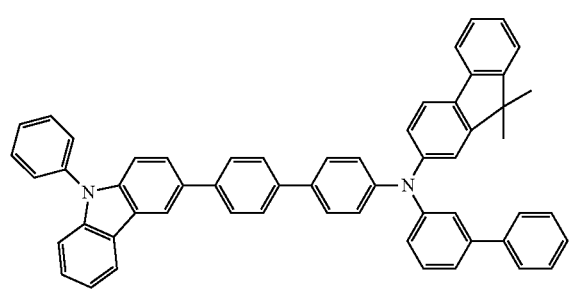
Chemical Formula 2-8
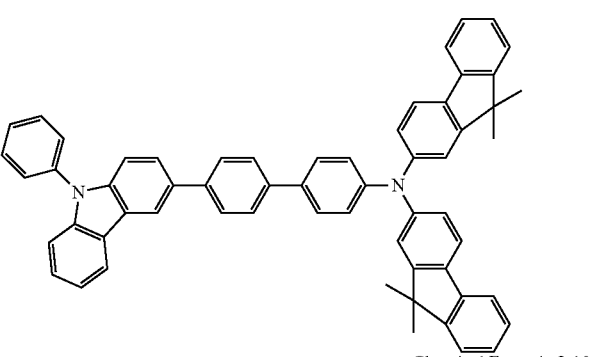
Chemical Formula 2-9
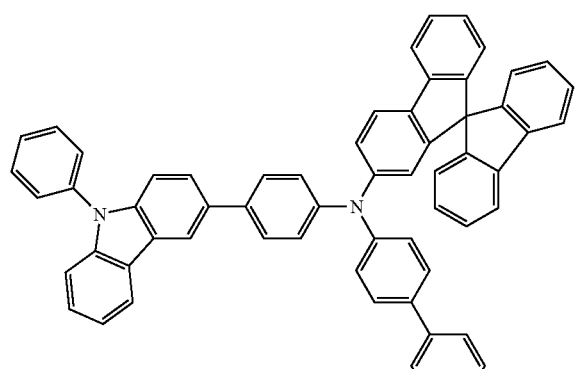
Chemical Formula 2-10
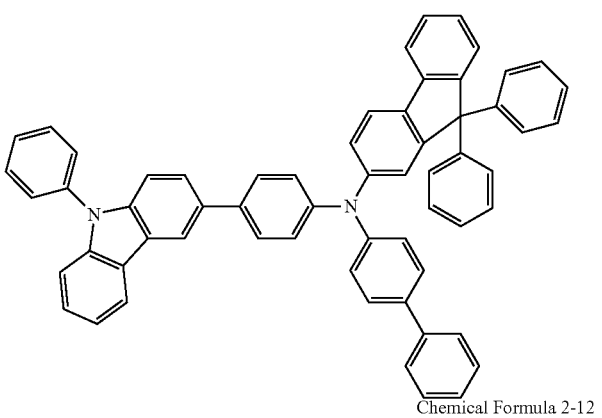
Chemical Formula 2-11
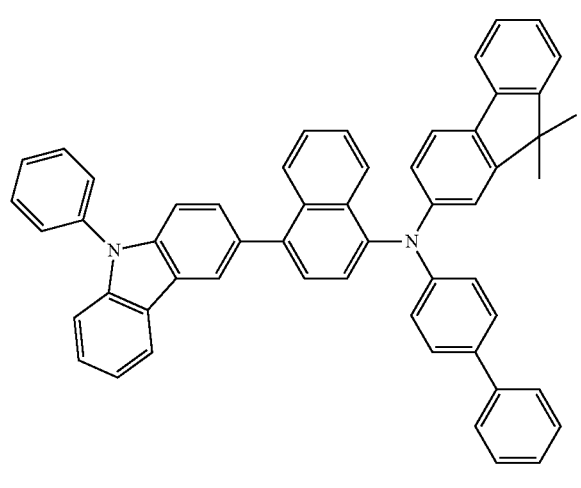
Chemical Formula 2-12
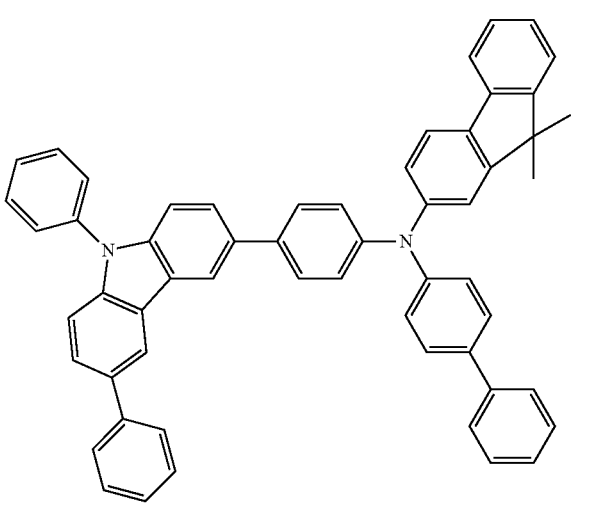

Chemical Formula 2-13
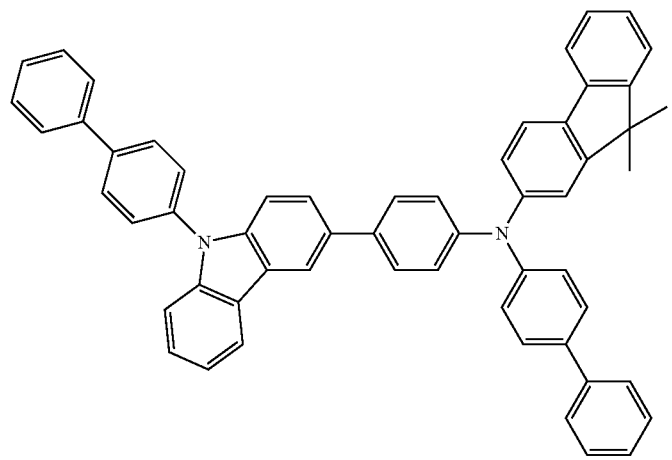
Chemical Formula 2-14
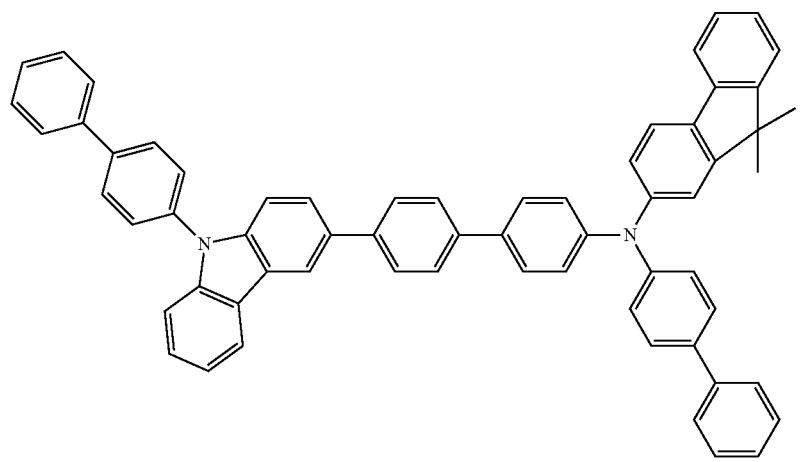
Chemical Formula 2-15
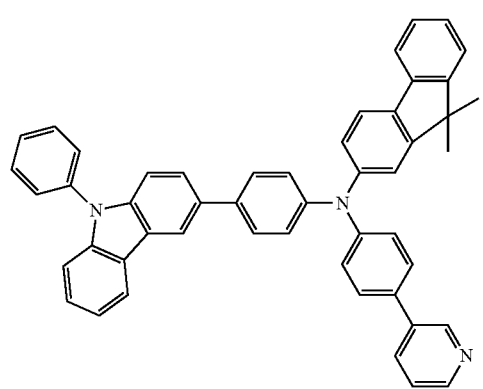
Chemical Formula 2-16
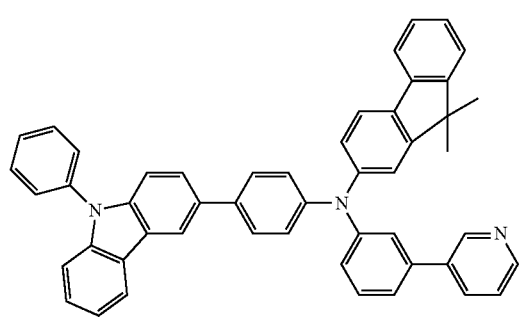

-continued

Chemical Formula 2-17

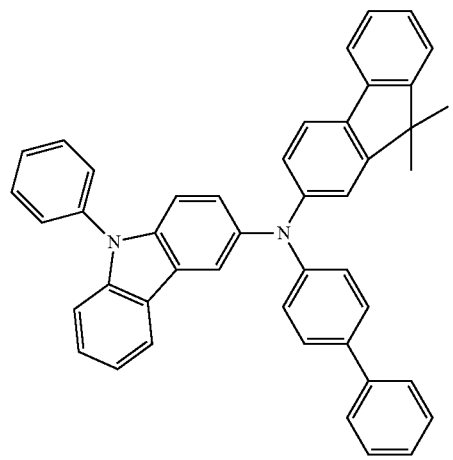

Chemical Formula 2-18

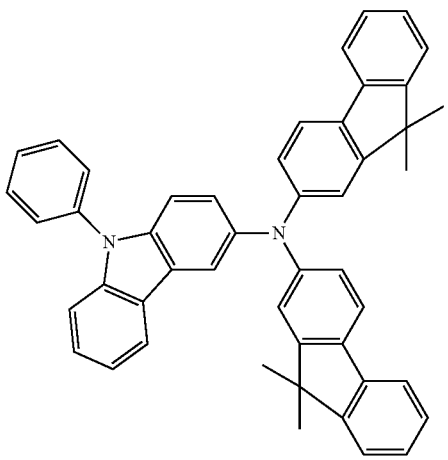

Chemical Formula 2-19

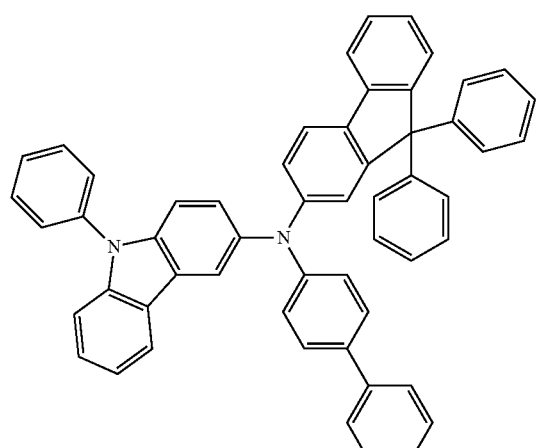

Chemical Formula 2-20

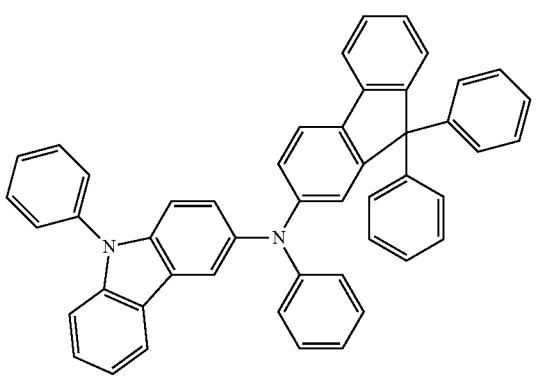

Chemical Formula 2-21

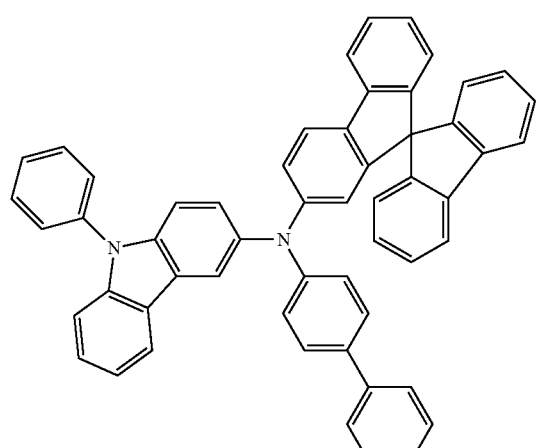

Chemical Formula 2-22

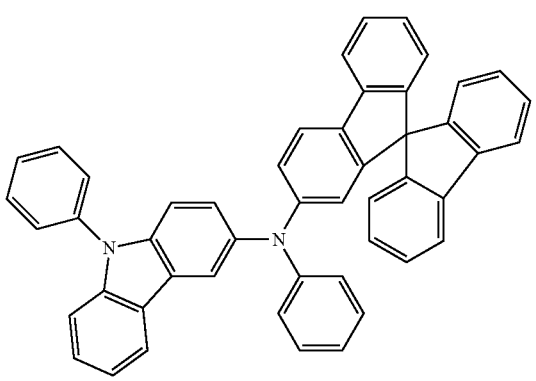

In the exemplary embodiment of the present specification, the organic material layer including the compound represented by Chemical Formula 1 is the electron transport layer, the compound represented by Chemical Formula 1 is represented by Chemical Formula 1-1-19, the organic material layer including the compound represented by Chemical Formula 2 is the hole transport layer, and the compound represented by Chemical Formula 2 is represented by Chemical Formula 2-3.

The organic light emitting diode of the present specification may be manufactured by a material and a method known in the art, except that the electron transport layer and the hole transport layer are included.

For example, the organic light emitting diode of the present specification may be manufactured by sequentially laminating the anode, the organic material layer, and the cathode on the substrate. In this case, the organic light emitting diode may be manufactured by depositing a metal, metal oxides having conductivity, or an alloy thereof on the substrate by using a physical vapor deposition (PVD) method such as a sputtering method or an e-beam evaporation method to form the anode, forming the organic material layer including the hole injection layer, the hole transport layer, the electron blocking layer, the light emitting layer, the electron transport layer, and the electron injection layer thereon, and then depositing a material that can be used as the cathode thereon. In addition to the aforementioned method, the organic light emitting diode may be manufactured by sequentially depositing a cathode material, the organic material layer, and an anode material on the substrate. In addition to the aforementioned method, the organic light emitting diode may be manufactured by sequentially depositing the anode material, the organic material layer, and the cathode material on the substrate.

The organic material layer of the organic light emitting diode of the present specification may have a multilayered structure where one or more organic material layers are laminated.

In the exemplary embodiment of the present specification, the organic light emitting diode may further include one layer or two or more layers selected from the group consisting of the hole injection layer, the hole transport layer, the electron transport layer, the electron injection layer, the electron blocking layer, and the hole blocking layer.

Figure 2:
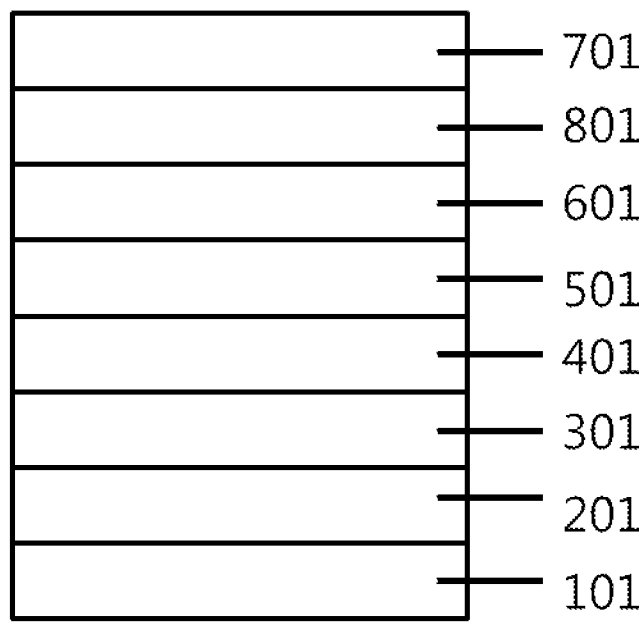
FIG. 2 illustrates an example of an organic light emitting diode according to an exemplary embodiment of the present specification.

For example, the structure of the organic light emitting diode of the present specification may have a structure shown in FIGS. 1 and 2, but is not limited thereto.

FIG. 1 illustrates a structure of an organic light emitting diode where an anode 201, a hole transport layer 301, an electron blocking layer 401, a light emitting layer 501, an electron transport layer 601, and a cathode 701 are sequentially laminated on a substrate 101. In FIG. 1, the compound represented by Chemical Formula 2 is included in the hole transport layer 301, and the compound represented by Chemical Formula 1 is included in the electron transport layer 601.

FIG. 2 illustrates a structure of an organic light emitting diode where the anode 201, the hole transport layer 301, the electron blocking layer 401, the light emitting layer 501, the electron transport layer 601, an electron injection layer 801, and the cathode 701 are sequentially laminated on the substrate 101. In FIG. 2, the compound represented by Chemical Formula 2 may be included in the hole transport layer 301, and the compound represented by Chemical Formula 1 may be included in the electron transport layer 601. Further, the compound represented by Chemical Formula 2 may be included in the hole transport layer 301, and the compound represented by Chemical Formula 1 may be included in the electron injection layer 801. Further, the compound represented by Chemical Formula 2 may be included in the hole transport layer 301, and the compound represented by Chemical Formula 1 may be included in the electron transport layer 601 and the electron injection layer 801.

FIGS. 1 and 2 are the exemplified structures according to the exemplary embodiment of the present specification, and may further include other organic material layers.

In the case where the organic light emitting diode includes a plurality of organic material layers, the organic material layers may be formed of the same material or different materials.

As the anode material, in general, it is preferable to use a material having a large work function so as to smoothly inject holes into the organic material layer. Specific examples of the anode material that may be used in the present invention include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or SNO$_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

It is preferable that the cathode material be, in general, a material having a small work function so as to easily inject electrons into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or LiO$_2$/Al, and the like, but are not limited thereto.

The hole injection material is a layer injecting the holes from the electrode, and it is preferable that the hole injection material be a compound which has an ability of transporting the holes to have a hole injection effect from the anode and an excellent hole injection effect to the light emitting layer or the light emitting material, prevents movement of an exciton generated in the light emitting layer to the electron injection layer or the electron injection material, and has an excellent thin film forming ability. It is preferable that a highest occupied molecular orbital (HOMO) of the hole injection material be between the work function of the anode material and a highest occupied molecular orbital (HOMO) of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline, a polythiophene-based conductive polymer, and the like, but are not limited thereto.

The electron blocking layer is a layer which may prevent the holes injected from the hole injection layer from moving into the electron injection layer via the light emitting layer to improve a life-span and efficiency of the diode, and if necessary, may be formed in an appropriate portion between the light emitting layer and the electron injection layer by using a publicly known material.

The light emitting material is a material that receives and combines the holes and the electrons from the hole transport layer and the electron transport layer, such that light in a visible light region is emitted, and it is preferable to use a material having excellent quantum efficiency to fluorescence or phosphorescence. Specific examples thereof include a 8-hydroxy-quinoline aluminum complex (Alq$_3$); a carbazole-based compound; a dimerized styryl compound; BAlq; a 10-hydroxybenzoquinoline-metal compound; benzoxazole, benzthiazole, and benzimidazole-based compounds; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensation aromatic ring derivative, a hetero-ring-containing compound, or the like. Specific examples of the compensation aromatic ring derivative include an anthracene derivative, a pyrene derivative, a naphthalene derivative, a pentacene derivative, a phenanthrene compound, a fluoranthene compound, and the like, and specific examples of the hetero-ring-containing compound include a carbazole derivative, a dibenzofuran derivative, a ladder-type furan compound, a pyrimidine derivative, and the like, but the examples are not limited thereto.

Examples of the dopant material include an organic compound, a metal, or a metal compound.

Examples of the organic compound as the dopant material include an aromatic amine derivative, a styrylamine compound, a boron complex, a fluoranthene compound, and the like. Specifically, the aromatic amine derivative is a compensation aromatic ring derivative having a substituted or unsubstituted arylamino group, examples thereof include pyrene, anthracene, chrysene, and periflanthene having the arylamino group, the styrylamine compound is a compound where at least one arylvinyl group is substituted in substituted or unsubstituted arylamine, and in the styrylamine compound, one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetraamine, and the like, but are not limited thereto. Further, a general metal or metal compound may be used as the metal or the metal compound, and specifically, a metal complex may be used. Further, examples of the metal complex include an iridium complex, a platinum complex, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The electron injection layer is a layer injecting the electrons from the electrode, and a compound which has an ability of transporting the electrons, an electron injection effect from the cathode, and an excellent electron injection effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The hole blocking layer is a layer preventing holes from reaching the cathode, and in general, may be formed under the same condition as the hole injection layer. Specific examples thereof include an oxadiazole derivative, a triazole derivative, a phenanthroline derivative, 2,9-dimethyl-4,7-diphenyl-1,10-phenanthroline (BCP), an aluminum complex, and the like, but are not limited thereto.

The organic light emitting diode according to the present specification may be a top emission type, a bottom emission type, or a both-sided emission type according to the used material.

Further, the organic light emitting diode according to the present specification may be a normal type where a lower electrode is the anode and an upper electrode is the cathode, or may be an inverted type where the lower electrode is the cathode and the upper electrode is the anode.

The structure according to the exemplary embodiment of the present specification may act even in an organic electronic diode including an organic solar cell, an organic photoconductor, an organic transistor, and the like by the principle that is similar to the principle applied to the organic light emitting diode.

Hereinafter, the present specification will be described in detail through Examples. However, the Examples according to the present specification may be modified in various other forms, and the scope of the present specification is not interpreted to be limited to the Examples described in detail below. The Examples of the present specification are provided so that a person with ordinary skill in the art may fully understand the present specification.

EXAMPLE

Example 1

Manufacturing of Organic Light Emitting Diode

The glass substrate (corning 7059 glass) on which the thin film of ITO (indium tin oxide) was applied at a thickness of 1,000 Å was immersed in distilled water having the detergent dissolved therein, and washed by the ultrasonic wave. In this case, the detergent used herein was the product commercially available from Fischer Co. and distilled water used herein was one which had been twice filtered by using the filter commercially available from Millipore Co. ITO was washed for 30 minutes, and washing with ultrasonic waves was then repeated twice for 10 minutes by using distilled water. After the completion of washing with distilled water, washing with ultrasonic waves was performed by using solvents such as isopropyl alcohol, acetone, and methanol, and the resulting product was dried and transported to the plasma washing machine. Further, the substrate was dry-washed by using the oxygen plasma for 5 minutes, and then transported to the vacuum deposition machine.

Hexanitrile hexaazatriphenylene (hereinafter, referred to as "HAT") that was the compound of the following Chemical Formula was deposited under the heat vacuum in a thickness of 500 Å on the prepared ITO transparent electrode to form the thin film. The interfacial property between the substrate and the hole injection layer can be improved by this thin film. Subsequently, the compound of Chemical Formula 2-3 was deposited in a thickness of 400 Å on the thin film to form the hole transport layer, and the compound of the following EB-1 was deposited in a thickness of 250

Å thereon to form the electron blocking layer. The compound of the following H1 as the host of the light emitting layer and the compound of the following D1 as the dopant were deposited under the vacuum in a thickness of 200 Å thereon. The electron transport layer material of Chemical Formula 1-1-1 and lithium quinolate (LiQ) were deposited under vacuum as at a weight ratio of 1:1 on the light emitting layer to form the electronic injection and transport layer in a thickness of 300 Å. Lithium fluoride (LiF) in a thickness of 12 Å and aluminum in a thickness of 2,000 Å were subsequently deposited on the electron transport layer to form the cathode.

In the aforementioned process, the deposition rate of the organic material was maintained at 0.3 to 0.8 Å/sec. Further, the deposition rate of lithium fluoride of the cathode was maintained at 0.3 Å/sec, and the deposition rate of aluminum was maintained at 1.5 to 2.5 Å/sec. The degree of vacuum during deposition was maintained at 1 to $3 \times 10^{-7}$.

[HAT]

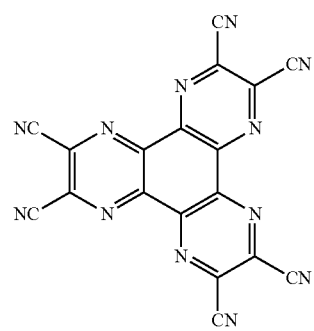

[LiQ]

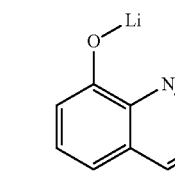

[H1]

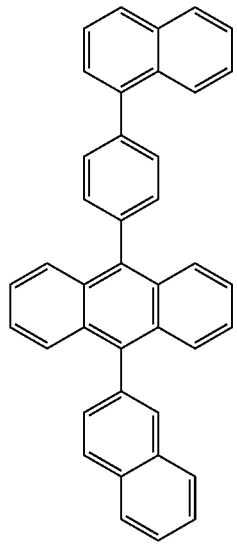

[D1]

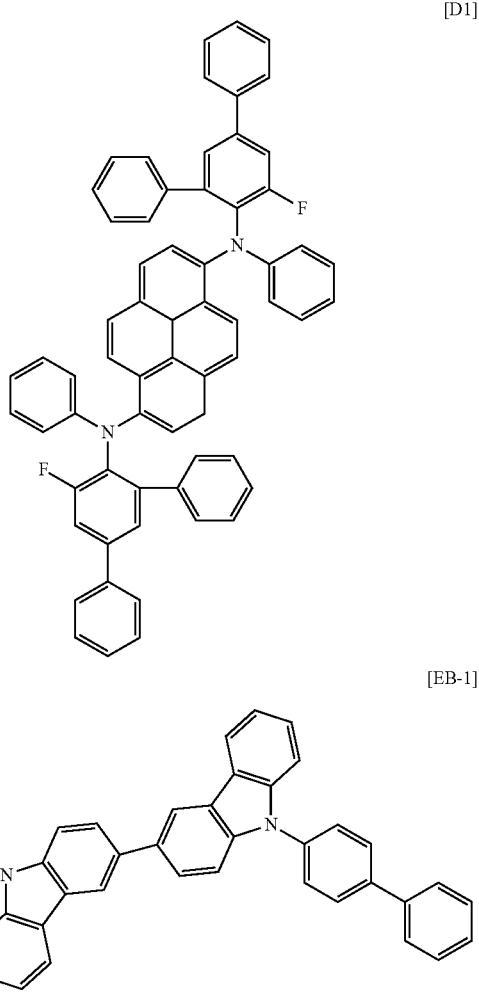

[EB-1]

Example 2

Manufacturing of Organic Light Emitting Diode

The organic light emitting diode was manufactured by the same method as Example 1, except that Chemical Formula 2-6 was used instead of Chemical Formula 2-3 in Example 1.

Example 3

Manufacturing of Organic Light Emitting Diode

The organic light emitting diode was manufactured by the same method as Example 1, except that Chemical Formula 2-13 was used instead of Chemical Formula 2-3 in Example 1.

Example 4

Manufacturing of Organic Light Emitting Diode

The organic light emitting diode was manufactured by the same method as Example 1, except that Chemical Formula 2-17 was used instead of Chemical Formula 2-3 in Example 1.

Example 5

Manufacturing of Organic Light Emitting Diode

The organic light emitting diode was manufactured by the same method as Example 1, except that Chemical Formula 1-1-2 was used instead of Chemical Formula 1-1-1 in Example 1.

Example 6

Manufacturing of Organic Light Emitting Diode

The organic light emitting diode was manufactured by the same method as Example 2, except that Chemical Formula 1-1-2 was used instead of Chemical Formula 1-1-1 in Example 2.

Example 7

Manufacturing of Organic Light Emitting Diode

The organic light emitting diode was manufactured by the same method as Example 3, except that Chemical Formula 1-1-2 was used instead of Chemical Formula 1-1-1 in Example 3.

Example 8

Manufacturing of Organic Light Emitting Diode

The organic light emitting diode was manufactured by the same method as Example 4, except that Chemical Formula 1-1-2 was used instead of Chemical Formula 1-1-1 in Example 4.

Example 9

Manufacturing of Organic Light Emitting Diode

The organic light emitting diode was manufactured by the same method as Example 1, except that Chemical Formula 1-1-27 was used instead of Chemical Formula 1-1-1 in Example 1.

Example 10

Manufacturing of Organic Light Emitting Diode

The organic light emitting diode was manufactured by the same method as Example 2, except that Chemical Formula 1-1-27 was used instead of Chemical Formula 1-1-1 in Example 2.

Example 11

Manufacturing of Organic Light Emitting Diode

The organic light emitting diode was manufactured by the same method as Example 3, except that Chemical Formula 1-1-27 was used instead of Chemical Formula 1-1-1 in Example 3.

Example 12

Manufacturing of Organic Light Emitting Diode

The organic light emitting diode was manufactured by the same method as Example 4, except that Chemical Formula 1-1-27 was used instead of Chemical Formula 1-1-1 in Example 4.

Example 13

Manufacturing of Organic Light Emitting Diode

The organic light emitting diode was manufactured by the same method as Example 1, except that Chemical Formula 1-1-17 was used instead of Chemical Formula 1-1-1 in Example 1.

Example 14

Manufacturing of Organic Light Emitting Diode

The organic light emitting diode was manufactured by the same method as Example 2, except that Chemical Formula 1-1-17 was used instead of Chemical Formula 1-1-1 in Example 2.

Example 15

Manufacturing of Organic Light Emitting Diode

The organic light emitting diode was manufactured by the same method as Example 3, except that Chemical Formula 1-1-17 was used instead of Chemical Formula 1-1-1 in Example 3.

Example 16

Manufacturing of Organic Light Emitting Diode

The organic light emitting diode was manufactured by the same method as Example 4, except that Chemical Formula 1-1-17 was used instead of Chemical Formula 1-1-1 in Example 4.

Example 17

Manufacturing of Organic Light Emitting Diode

The organic light emitting diode was manufactured by the same method as Example 1, except that Chemical Formula 1-1-19 was used instead of Chemical Formula 1-1-1 in Example 1.

Example 18

Manufacturing of Organic Light Emitting Diode

The organic light emitting diode was manufactured by the same method as Example 2, except that Chemical Formula 1-1-19 was used instead of Chemical Formula 1-1-1 in Example 2.

Example 19

Manufacturing of Organic Light Emitting Diode

The organic light emitting diode was manufactured by the same method as Example 3, except that Chemical Formula 1-1-19 was used instead of Chemical Formula 1-1-1 in Example 3.

Example 20

Manufacturing of Organic Light Emitting Diode

The organic light emitting diode was manufactured by the same method as Example 4, except that Chemical Formula 1-1-19 was used instead of Chemical Formula 1-1-1 in Example 4.

Example 21

Manufacturing of Organic Light Emitting Diode

The organic light emitting diode was manufactured by the same method as Example 1, except that Chemical Formula 1-4-4 was used instead of Chemical Formula 1-1-1 in Example 1.

Example 22

Manufacturing of Organic Light Emitting Diode

The organic light emitting diode was manufactured by the same method as Example 2, except that Chemical Formula 1-4-4 was used instead of Chemical Formula 1-1-1 in Example 2.

Example 23

Manufacturing of Organic Light Emitting Diode

The organic light emitting diode was manufactured by the same method as Example 3, except that Chemical Formula 1-4-4 was used instead of Chemical Formula 1-1-1 in Example 3.

Example 24

Manufacturing of Organic Light Emitting Diode

The organic light emitting diode was manufactured by the same method as Example 4, except that Chemical Formula 1-4-4 was used instead of Chemical Formula 1-1-1 in Example 4.

Comparative Example 1

Manufacturing of Organic Light Emitting Diode

The organic light emitting diode was manufactured by the same method as Example 1, except that the following Chemical Formula ET-1 was used instead of Chemical Formula 1-1-1 in Example 1.

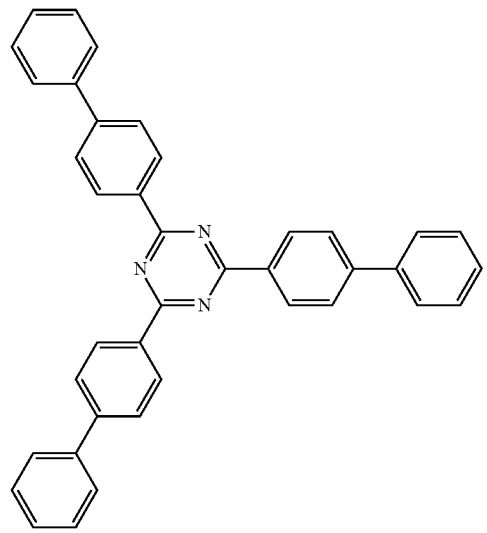

[ET-1]

Comparative Example 2

Manufacturing of Organic Light Emitting Diode

The organic light emitting diode was manufactured by the same method as Example 2, except that Chemical Formula ET-1 was used instead of Chemical Formula 1-1-1 in Example 2.

Comparative Example 3

Manufacturing of Organic Light Emitting Diode

The organic light emitting diode was manufactured by the same method as Example 3, except that Chemical Formula ET-1 was used instead of Chemical Formula 1-1-1 in Example 3.

Comparative Example 4

Manufacturing of Organic Light Emitting Diode

The organic light emitting diode was manufactured by the same method as Example 4, except that Chemical Formula ET-1 was used instead of Chemical Formula 1-1-1 in Example 4.

Comparative Example 5

Manufacturing of Organic Light Emitting Diode

The organic light emitting diode was manufactured by the same method as Example 1, except that the following Chemical Formula ET-2 was used instead of Chemical Formula 1-1-1 in Example 1.

[ET-2]

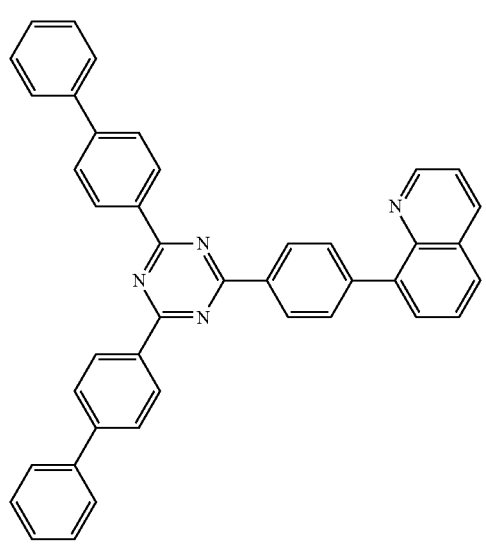

[ET-3]

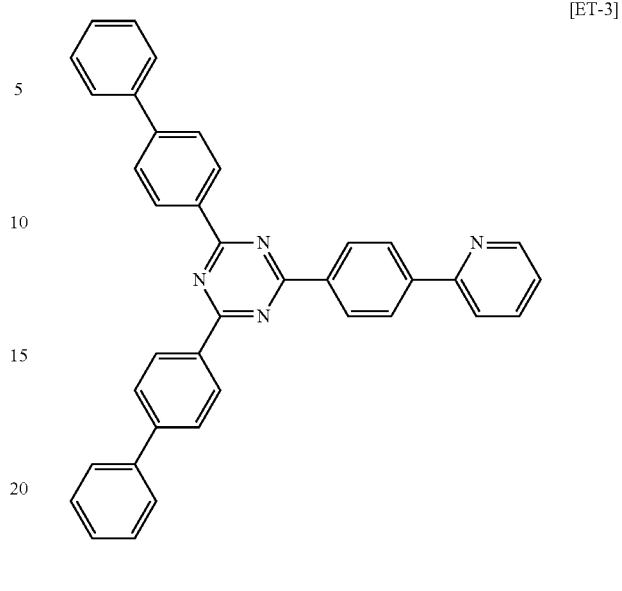

Comparative Example 6

Manufacturing of Organic Light Emitting Diode

The organic light emitting diode was manufactured by the same method as Example 2, except that Chemical Formula ET-2 was used instead of Chemical Formula 1-1-1 in Example 2.

Comparative Example 7

Manufacturing of Organic Light Emitting Diode

The organic light emitting diode was manufactured by the same method as Example 3, except that Chemical Formula ET-2 was used instead of Chemical Formula 1-1-1 in Example 3.

Comparative Example 8

Manufacturing of Organic Light Emitting Diode

The organic light emitting diode was manufactured by the same method as Example 4, except that Chemical Formula ET-2 was used instead of Chemical Formula 1-1-1 in Example 4.

Comparative Example 9

Manufacturing of Organic Light Emitting Diode

The organic light emitting diode was manufactured by the same method as Example 1, except that the following Chemical Formula ET-3 was used instead of Chemical Formula 1-1-1 in Example 1.

Comparative Example 10

Manufacturing of Organic Light Emitting Diode

The organic light emitting diode was manufactured by the same method as Example 2, except that Chemical Formula ET-3 was used instead of Chemical Formula 1-1-1 in Example 2.

Comparative Example 11

Manufacturing of Organic Light Emitting Diode

The organic light emitting diode was manufactured by the same method as Example 3, except that Chemical Formula ET-3 was used instead of Chemical Formula 1-1-1 in Example 3.

Comparative Example 12

Manufacturing of Organic Light Emitting Diode

The organic light emitting diode was manufactured by the same method as Example 4, except that Chemical Formula ET-3 was used instead of Chemical Formula 1-1-1 in Example 4.

Comparative Example 13

Manufacturing of Organic Light Emitting Diode

The organic light emitting diode was manufactured by the same method as Example 1, except that the following Chemical Formula ET-4 was used instead of Chemical Formula 1-1-1 in Example 1.

[ET-4]

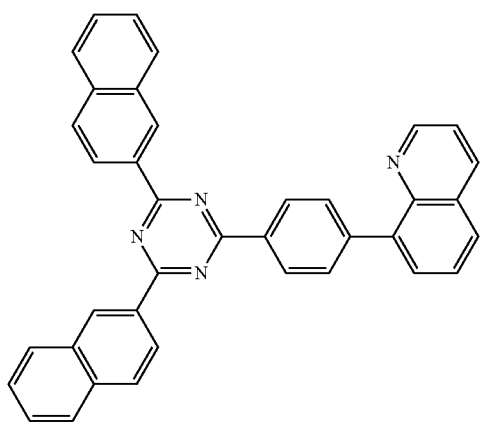

Comparative Example 14

Manufacturing of Organic Light Emitting Diode

The organic light emitting diode was manufactured by the same method as Example 2, except that Chemical Formula ET-4 was used instead of Chemical Formula 1-1-1 in Example 2.

Comparative Example 15

Manufacturing of Organic Light Emitting Diode

The organic light emitting diode was manufactured by the same method as Example 3, except that Chemical Formula ET-4 was used instead of Chemical Formula 1-1-1 in Example 3.

Comparative Example 16

Manufacturing of Organic Light Emitting Diode

The organic light emitting diode was manufactured by the same method as Example 4, except that Chemical Formula ET-4 was used instead of Chemical Formula 1-1-1 in Example 4.

Comparative Example 17

Manufacturing of Organic Light Emitting Diode

The organic light emitting diode was manufactured by the same method as Example 1, except that the following Chemical Formula ET-5 was used instead of Chemical Formula 1-1-1 in Example 1.

[ET-5]

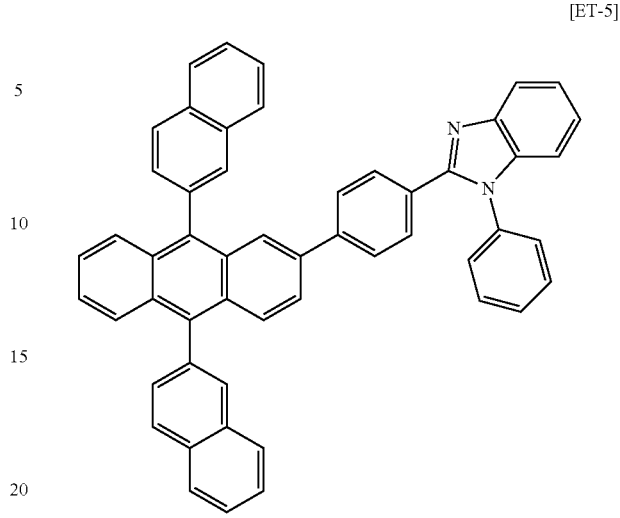

Comparative Example 18

Manufacturing of Organic Light Emitting Diode

The organic light emitting diode was manufactured by the same method as Example 2, except that Chemical Formula ET-5 was used instead of Chemical Formula 1-1-1 in Example 2.

Comparative Example 19

Manufacturing of Organic Light Emitting Diode

The organic light emitting diode was manufactured by the same method as Example 3, except that Chemical Formula ET-5 was used instead of Chemical Formula 1-1-1 in Example 3.

Comparative Example 20

Manufacturing of Organic Light Emitting Diode

The organic light emitting diode was manufactured by the same method as Example 4, except that Chemical Formula ET-5 was used instead of Chemical Formula 1-1-1 in Example 4.

Comparative Example 21

Manufacturing of Organic Light Emitting Diode

The organic light emitting diode was manufactured by the same method as Example 1, except that the following Chemical Formula ET-6 was used instead of Chemical Formula 1-1-1 in Example 1.

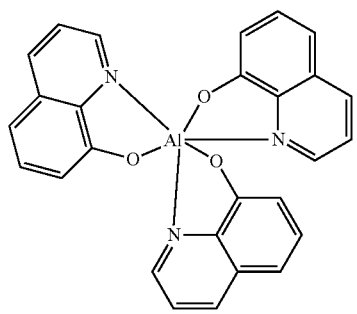

[ET-6]

Comparative Example 22

Manufacturing of Organic Light Emitting Diode

The organic light emitting diode was manufactured by the same method as Example 2, except that Chemical Formula ET-6 was used instead of Chemical Formula 1-1-1 in Example 2.

Comparative Example 23

Manufacturing of Organic Light Emitting Diode

The organic light emitting diode was manufactured by the same method as Example 3, except that Chemical Formula ET-6 was used instead of Chemical Formula 1-1-1 in Example 3.

Comparative Example 24

Manufacturing of Organic Light Emitting Diode

The organic light emitting diode was manufactured by the same method as Example 4, except that Chemical Formula ET-6 was used instead of Chemical Formula 1-1-1 in Example 4.

Comparative Example 25

Manufacturing of Organic Light Emitting Diode

The organic light emitting diode was manufactured by the same method as Example 1, except that the following Chemical Formula HT-1 was used instead of Chemical Formula 2-3 in Example 1.

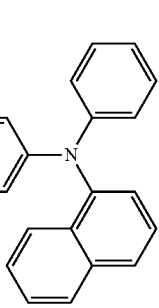

[HT-1]

Comparative Example 26

Manufacturing of Organic Light Emitting Diode

The organic light emitting diode was manufactured by the same method as Example 5, except that the following Chemical Formula HT-1 was used instead of Chemical Formula 2-3 in Example 5.

Comparative Example 27

Manufacturing of Organic Light Emitting Diode

The organic light emitting diode was manufactured by the same method as Example 9, except that Chemical Formula HT-1 was used instead of Chemical Formula 2-3 in Example 9.

Comparative Example 28

Manufacturing of Organic Light Emitting Diode

The organic light emitting diode was manufactured by the same method as Example 13, except that Chemical Formula HT-1 was used instead of Chemical Formula 2-3 in Example 13.

Comparative Example 29

Manufacturing of Organic Light Emitting Diode

The organic light emitting diode was manufactured by the same method as Example 17, except that Chemical Formula HT-1 was used instead of Chemical Formula 2-3 in Example 17.

Comparative Example 30

Manufacturing of Organic Light Emitting Diode

The organic light emitting diode was manufactured by the same method as Example 21, except that Chemical Formula HT-1 was used instead of Chemical Formula 2-3 in Example 21.

Comparative Example 31

Manufacturing of Organic Light Emitting Diode

The organic light emitting diode was manufactured by the same method as Example 1, except that the following Chemical Formula HT-2 was used instead of Chemical Formula 2-3 in Example 1.

[HT-2]

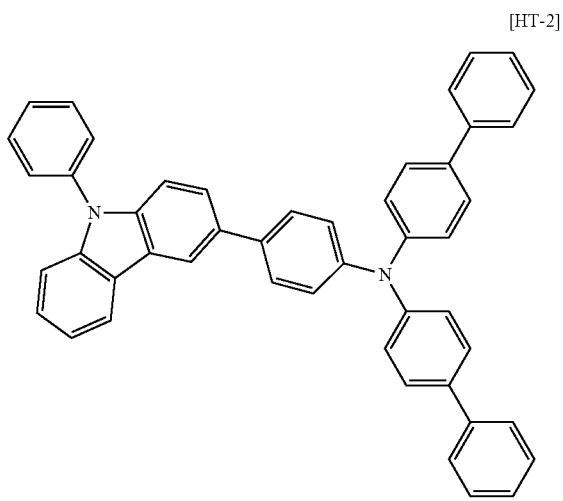 [SMILES: c1ccc(-c2ccc(N(c3ccc(-c4ccccc4)cc3)c3ccc(-c4ccc5c(c4)c4ccccc4n5-c4ccccc4)cc3)cc2)cc1]

Comparative Example 32

Manufacturing of Organic Light Emitting Diode

The organic light emitting diode was manufactured by the same method as Example 5, except that the following Chemical Formula HT-2 was used instead of Chemical Formula 2-3 in Example 5.

Comparative Example 33

Manufacturing of Organic Light Emitting Diode

The organic light emitting diode was manufactured by the same method as Example 9, except that the following Chemical Formula HT-2 was used instead of Chemical Formula 2-3 in Example 9.

Comparative Example 34

Manufacturing of Organic Light Emitting Diode

The organic light emitting diode was manufactured by the same method as Example 13, except that the following Chemical Formula HT-2 was used instead of Chemical Formula 2-3 in Example 13.

Comparative Example 35

Manufacturing of Organic Light Emitting Diode

The organic light emitting diode was manufactured by the same method as Example 17, except that the following Chemical Formula HT-2 was used instead of Chemical Formula 2-3 in Example 17.

Comparative Example 36

Manufacturing of Organic Light Emitting Diode

The organic light emitting diode was manufactured by the same method as Example 21, except that the following Chemical Formula HT-2 was used instead of Chemical Formula 2-3 in Example 21.

Comparative Example 37

Manufacturing of Organic Light Emitting Diode

The organic light emitting diode was manufactured by the same method as Example 1, except that the compound of ET-1 and Chemical Formula HT-1 were used instead of Chemical Formula 1-1-1 and Chemical Formula 2-3 in Example 1.

Comparative Example 38

Manufacturing of Organic Light Emitting Diode

The organic light emitting diode was manufactured by the same method as Example 1, except that the compound of ET-1 and Chemical Formula HT-2 were used instead of Chemical Formula 1-1-1 and Chemical Formula 2-3 in Example 1.

Comparative Example 39

Manufacturing of Organic Light Emitting Diode

The organic light emitting diode was manufactured by the same method as Example 1, except that the compound of ET-2 and Chemical Formula HT-1 were used instead of Chemical Formula 1-1-1 and Chemical Formula 2-3 in Example 1.

Comparative Example 40

Manufacturing of Organic Light Emitting Diode

The organic light emitting diode was manufactured by the same method as Example 1, except that the compound of ET-2 and Chemical Formula HT-2 were used instead of Chemical Formula 1-1-1 and Chemical Formula 2-3 in Example 1.

Comparative Example 41

Manufacturing of Organic Light Emitting Diode

The organic light emitting diode was manufactured by the same method as Example 1, except that the compound of ET-3 and Chemical Formula HT-1 were used instead of Chemical Formula 1-1-1 and Chemical Formula 2-3 in Example 1.

Comparative Example 42

Manufacturing of Organic Light Emitting Diode

The organic light emitting diode was manufactured by the same method as Example 1, except that the compound of ET-3 was used instead of Chemical Formula 1-1-1 and Chemical Formula HT-2 was used instead of Chemical Formula 2-3 in Example 1.

Comparative Example 43

Manufacturing of Organic Light Emitting Diode

The organic light emitting diode was manufactured by the same method as Example 1, except that the compound of ET-4 and Chemical Formula HT-1 were used instead of Chemical Formula 1-1-1 and Chemical Formula 2-3 in Example 1.

Comparative Example 44

Manufacturing of Organic Light Emitting Diode

The organic light emitting diode was manufactured by the same method as Example 1, except that the compound of ET-4 and Chemical Formula HT-2 were used instead of Chemical Formula 1-1-1 and Chemical Formula 2-3 in Example 1.

Comparative Example 45

Manufacturing of Organic Light Emitting Diode

The organic light emitting diode was manufactured by the same method as Example 1, except that the compound of ET-5 and Chemical Formula HT-1 were used instead of Chemical Formula 1-1-1 and Chemical Formula 2-3 in Example 1.

Comparative Example 46

Manufacturing of Organic Light Emitting Diode

The organic light emitting diode was manufactured by the same method as Example 1, except that the compound of ET-5 and Chemical Formula HT-2 were used instead of Chemical Formula 1-1-1 and Chemical Formula 2-3 in Example 1.

Comparative Example 47

Manufacturing of Organic Light Emitting Diode

The organic light emitting diode was manufactured by the same method as Example 1, except that the compound of ET-6 and Chemical Formula HT-1 were used instead of Chemical Formula 1-1-1 and Chemical Formula 2-3 in Example 1.

Comparative Example 48

Manufacturing of Organic Light Emitting Diode

The organic light emitting diode was manufactured by the same method as Example 1, except that the compound of ET-6 and Chemical Formula HT-2 were used instead of Chemical Formula 1-1-1 and Chemical Formula 2-3 in Example 1.

Comparative Example 49

Manufacturing of Organic Light Emitting Diode

The organic light emitting diode was manufactured by the same method as Example 1, except that the following Chemical Formula ET-7 was used instead of Chemical Formula 1-1-1 in Example 1.

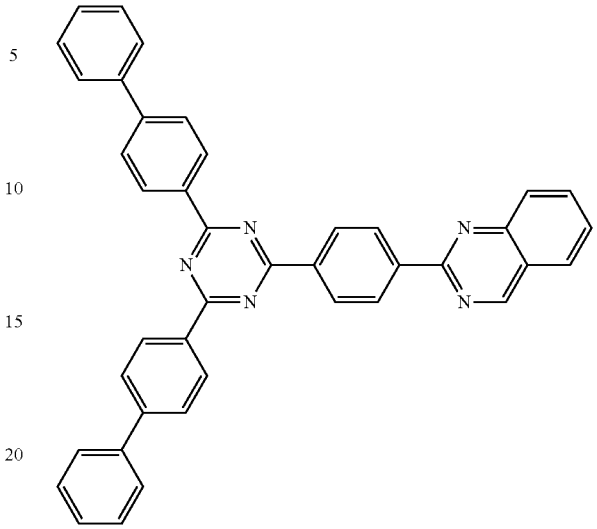

[ET-7]

Comparative Example 50

Manufacturing of Organic Light Emitting Diode

The organic light emitting diode was manufactured by the same method as Example 2, except that Chemical Formula ET-7 was used instead of Chemical Formula 1-1-1 in Example 2.

Comparative Example 51

Manufacturing of Organic Light Emitting Diode

The organic light emitting diode was manufactured by the same method as Example 3, except that Chemical Formula ET-7 was used instead of Chemical Formula 1-1-1 in Example 3.

Comparative Example 52

Manufacturing of Organic Light Emitting Diode

The organic light emitting diode was manufactured by the same method as Example 4, except that Chemical Formula ET-7 was used instead of Chemical Formula 1-1-1 in Example 4.

The driving voltage and light emitting efficiency of the organic light emitting diode manufactured by the aforementioned method were measured at the current density of 10 mA/cm$^2$, and the time (LT98) at which brightness was 98% of initial brightness was measured at the current density of 20 mA/cm$^2$. The result is described in the following Table 1.

TABLE 1

| | Voltage (V) | Current efficiency (cd/A) | Color coordinates (x, y) | Life Time 98 at 20 mA/cm$^2$ |
|---|---|---|---|---|
| Experimental Example 1 | 4.01 | 5.54 | (0.138, 0.142) | 44 |
| Experimental Example 2 | 4.18 | 5.76 | (0.138, 0.142) | 40 |

TABLE 1-continued

| | Voltage (V) | Current efficiency (cd/A) | Color coordinates (x, y) | Life Time 98 at 20 mA/cm$^2$ |
|---|---|---|---|---|
| Experimental Example 3 | 4.05 | 5.56 | (0.138, 0.142) | 39 |
| Experimental Example 4 | 3.94 | 5.78 | (0.139, 0.143) | 35 |
| Experimental Example 5 | 3.99 | 5.52 | (0.138, 0.142) | 43 |
| Experimental Example 6 | 4.10 | 5.68 | (0.139, 0.142) | 41 |
| Experimental Example 7 | 4.01 | 5.58 | (0.138, 0.142) | 38 |
| Experimental Example 8 | 3.88 | 5.65 | (0.138, 0.143) | 34 |
| Experimental Example 9 | 4.11 | 5.64 | (0.138, 0.142) | 42 |
| Experimental Example 10 | 4.21 | 5.87 | (0.138, 0.143) | 41 |
| Experimental Example 11 | 4.07 | 5.66 | (0.138, 0.142) | 35 |
| Experimental Example 12 | 3.99 | 5.85 | (0.139, 0.142) | 31 |
| Experimental Example 13 | 4.10 | 5.55 | (0.138, 0.142) | 47 |
| Experimental Example 14 | 4.13 | 5.35 | (0.138, 0.142) | 48 |
| Experimental Example 15 | 4.04 | 5.79 | (0.138, 0.142) | 42 |
| Experimental Example 16 | 3.98 | 5.53 | (0.138, 0.142) | 33 |
| Experimental Example 17 | 4.02 | 5.44 | (0.138, 0.142) | 41 |
| Experimental Example 18 | 4.09 | 5.51 | (0.138, 0.142) | 42 |
| Experimental Example 19 | 4.07 | 5.35 | (0.138, 0.142) | 44 |
| Experimental Example 20 | 4.03 | 5.42 | (0.139, 0.143) | 45 |
| Experimental Example 21 | 4.01 | 5.77 | (0.138, 0.142) | 45 |
| Experimental Example 22 | 4.05 | 5.76 | (0.138, 0.142) | 48 |
| Experimental Example 23 | 4.02 | 5.76 | (0.138, 0.142) | 50 |
| Experimental Example 24 | 3.85 | 5.78 | (0.138, 0.142) | 49 |
| Comparative Example 1 | 4.05 | 5.14 | (0.138, 0.142) | 25 |
| Comparative Example 2 | 4.21 | 5.05 | (0.138, 0.142) | 21 |
| Comparative Example 3 | 4.11 | 5.01 | (0.138, 0.142) | 19 |
| Comparative Example 4 | 4.03 | 4.99 | (0.138, 0.143) | 22 |
| Comparative Example 5 | 4.03 | 5.11 | (0.138, 0.141) | 27 |
| Comparative Example 6 | 4.18 | 5.25 | (0.137, 0.142) | 30 |
| Comparative Example 7 | 4.09 | 5.16 | (0.138, 0.142) | 28 |
| Comparative Example 8 | 4.09 | 5.05 | (0.139, 0.142) | 26 |
| Comparative Example 9 | 4.04 | 4.84 | (0.138, 0.142) | 26 |
| Comparative Example 10 | 4.19 | 5.06 | (0.138, 0.142) | 22 |
| Comparative Example 11 | 4.11 | 5.03 | (0.138, 0.141) | 20 |
| Comparative Example 12 | 4.04 | 4.89 | (0.138, 0.142) | 20 |
| Comparative Example 13 | 4.20 | 5.31 | (0.138, 0.141) | 11 |
| Comparative Example 14 | 4.48 | 5.24 | (0.137, 0.142) | 8 |
| Comparative Example 15 | 4.39 | 5.06 | (0.138, 0.142) | 5 |
| Comparative Example 16 | 4.59 | 5.25 | (0.139, 0.143) | 9 |
| Comparative Example 17 | 4.00 | 5.05 | (0.138, 0.142) | 18 |
| Comparative Example 18 | 4.05 | 5.21 | (0.139, 0.142) | 19 |
| Comparative Example 19 | 4.04 | 5.25 | (0.138, 0.142) | 7 |
| Comparative Example 20 | 4.03 | 5.22 | (0.138, 0.142) | 15 |
| Comparative Example 21 | 4.42 | 4.14 | (0.138, 0.152) | 12 |
| Comparative Example 22 | 4.50 | 3.05 | (0.138, 0.146) | 15 |
| Comparative Example 23 | 5.11 | 4.05 | (0.138, 0.144) | 16 |
| Comparative Example 24 | 5.01 | 3.98 | (0.138, 0.142) | 11 |
| Comparative Example 25 | 4.51 | 5.02 | (0.138, 0.142) | 35 |
| Comparative Example 26 | 4.64 | 5.24 | (0.138, 0.142) | 23 |
| Comparative Example 27 | 4.60 | 5.05 | (0.138, 0.142) | 28 |
| Comparative Example 28 | 4.75 | 5.03 | (0.138, 0.141) | 14 |
| Comparative Example 29 | 4.55 | 5.01 | (0.138, 0.142) | 20 |
| Comparative Example 30 | 4.62 | 4.74 | (0.138, 0.142) | 21 |
| Comparative Example 31 | 4.44 | 5.10 | (0.138, 0.142) | 20 |
| Comparative Example 32 | 4.35 | 5.22 | (0.138, 0.142) | 19 |
| Comparative Example 33 | 4.50 | 5.15 | (0.138, 0.142) | 18 |
| Comparative Example 34 | 4.63 | 5.11 | (0.138, 0.141) | 15 |
| Comparative Example 35 | 4.45 | 5.01 | (0.138, 0.142) | 21 |
| Comparative Example 36 | 4.53 | 4.99 | (0.138, 0.142) | 16 |
| Comparative Example 37 | 4.45 | 5.02 | (0.138, 0.142) | 21 |
| Comparative Example 38 | 4.33 | 5.09 | (0.138, 0.141) | 19 |
| Comparative Example 39 | 4.34 | 4.80 | (0.138, 0.142) | 23 |
| Comparative Example 40 | 4.90 | 5.01 | (0.138, 0.144) | 12 |
| Comparative Example 41 | 4.20 | 5.06 | (0.138, 0.142) | 18 |
| Comparative Example 42 | 4.31 | 5.10 | (0.138, 0.142) | 12 |
| Comparative Example 43 | 4.35 | 4.91 | (0.139, 0.143) | 15 |
| Comparative Example 44 | 5.02 | 3.98 | (0.138, 0.142) | 13 |
| Comparative Example 45 | 4.86 | 5.00 | (0.138, 0.141) | 16 |
| Comparative Example 46 | 4.55 | 5.21 | (0.138, 0.142) | 21 |
| Comparative Example 47 | 4.80 | 5.05 | (0.138, 0.144) | 18 |
| Comparative Example 48 | 4.21 | 5.16 | (0.138, 0.142) | 17 |
| Comparative Example 49 | 4.57 | 5.30 | (0.138, 0.142) | 19 |
| Comparative Example 50 | 4.48 | 5.11 | (0.138, 0.142) | 14 |
| Comparative Example 51 | 4.68 | 5.02 | (0.138, 0.142) | 15 |
| Comparative Example 52 | 4.33 | 5.17 | (0.138, 0.142) | 21 |

As seen in Table 1, it can be confirmed that the organic light emitting diode using the compound represented by Chemical Formula 1 as the electron transport material according to the exemplary embodiment of the present specification has high efficiency, a low driving voltage, and a long life-span as compared to the case where an existing electron transport material is used.

This is because the compound represented by Chemical Formula 1 is a bipolar type including both a p type and an n type, so that hole leakage can be prevented and an exciton can be effectively confined in the light emitting layer.

The invention claimed is:

1. An organic light emitting diode comprising:

an anode;

a cathode;

a light emitting layer provided between the anode and the cathode;

an organic material layer including a compound represented by the following Chemical Formula 1 and provided between the cathode and the light emitting layer; and an organic material layer including a compound represented by the following Chemical Formula 2 and provided between the anode and the light emitting layer,

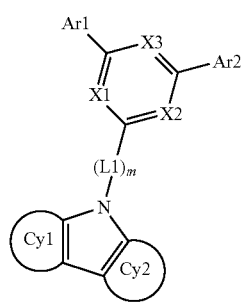

[Chemical Formula 1]

wherein in Chemical Formula 1,

X1 to X3 are the same as or different from each other, and are each independently N or CH, at least one of X1 to X3 is N, Cy1 and Cy2 are the same as or different from each other, and are each independently a benzene cycle; or a naphthalene cycle, at least one of Cy1 and Cy2 is benzene cycle, L1 is a phenylene group; a biphenylene group; or a terphenylene group, m is 1, Ar1 and Ar2 are the same as or different from each other, and are each independently a phenyl group; a phenyl group substituted by an alkyl group; a biphenyl group; or a naphthyl group, and

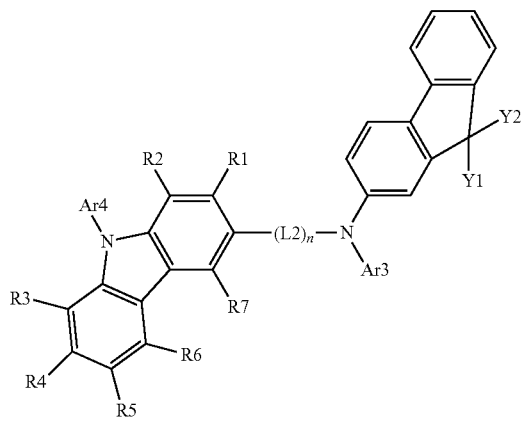

[Chemical Formula 2]

in Chemical Formula 2,

Ar3 and Ar4 are the same as or different from each other, and are a phenyl group; or a biphenyl group, L2 is a phenylene group; or a biphenylene group, n is an integer of 0 or 1, R1 to R7 are each independently hydrogen, and Y1 and Y2 are the same as or different from each other, and are each independently alkyl group, wherein the organic material layer including the compound represented by Chemical Formula 1 is an electron transport layer, an electron injection layer, or a layer simultaneously transporting and injecting electrons, and wherein the organic material layer including the compound represented by Chemical Formula 2 is a hole transport layer.

2. The organic light emitting diode of claim 1, further comprising:

one or two or more layers selected from the group consisting of an electron injection layer and an electron transport layer between the light emitting layer and the cathode.

3. The organic light emitting diode of claim 1, further comprising:

one or two or more layers selected from the group consisting of a hole transport layer, a hole injection layer, and an electron blocking layer between the light emitting layer and the anode.

4. The organic light emitting diode of claim 1, wherein the compound represented by Chemical Formula 1 is a compound represented by any one of the following Chemical Formulas 1-1 to 1-4:

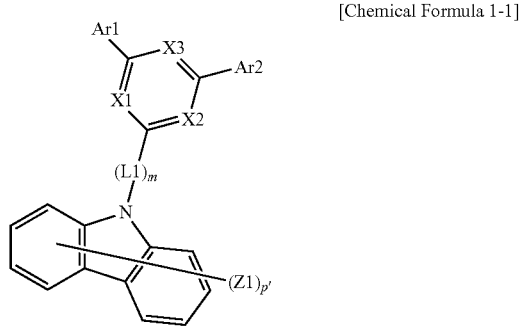

[Chemical Formula 1-1]

[Chemical Formula 1-2]

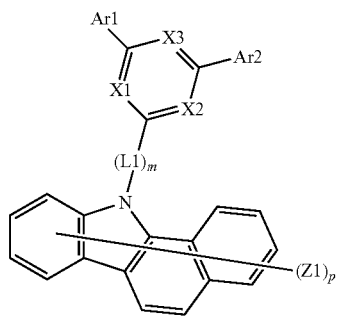

[Chemical Formula 1-3]

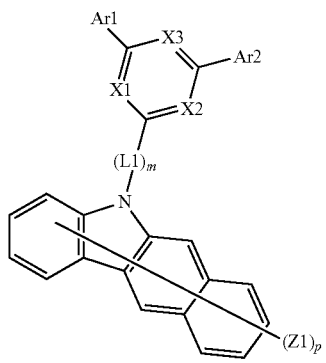

[Chemical Formula 1-4]

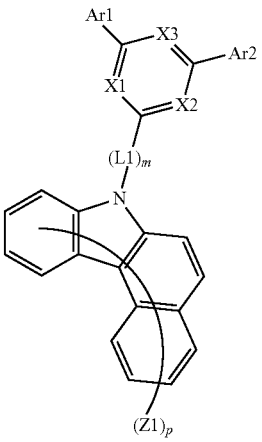

in Chemical Formulas 1-1 to 1-4,
X1 to X3, L1, m, Ar1, and Ar2 are the same as those defined in Chemical Formula 1,
Z1 is deuterium,
p' is 0, and
p is 0.

5. The organic light emitting diode of claim 1, wherein X1 to X3 are N.

6. The organic light emitting diode of claim 1, wherein the compound represented by Chemical Formula 1 is represented by any one of the following compounds:

Chemical Formula 1-1-1

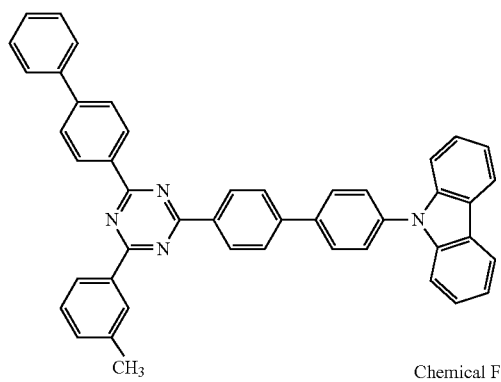

Chemical Formula 1-1-2

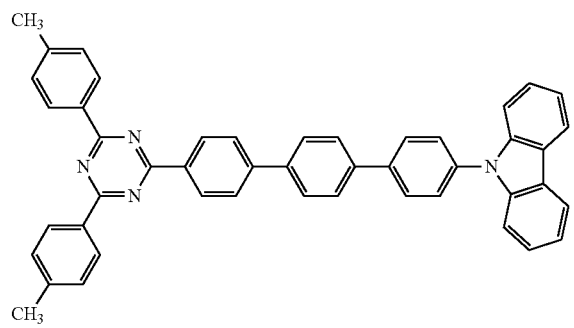

Chemical Formula 1-1-3

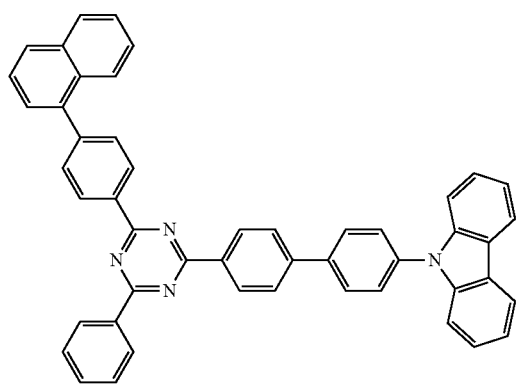

Chemical Formula 1-1-4

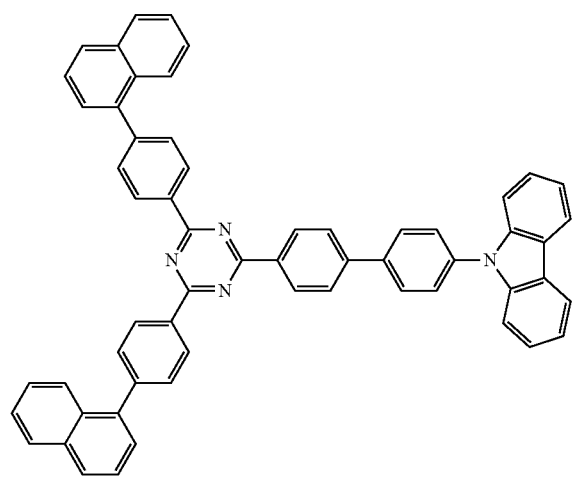

Chemical Formula 1-1-5
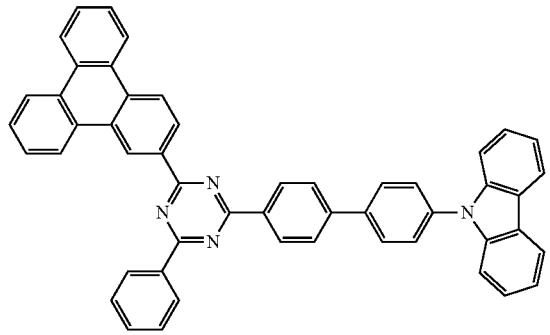
Chemical Formula 1-1-6
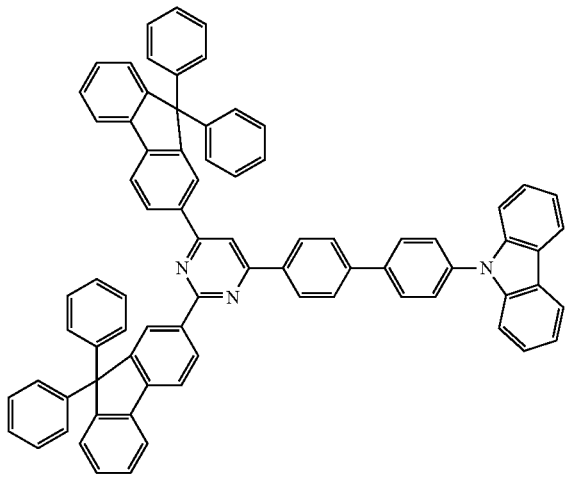
Chemical Formula 1-1-7
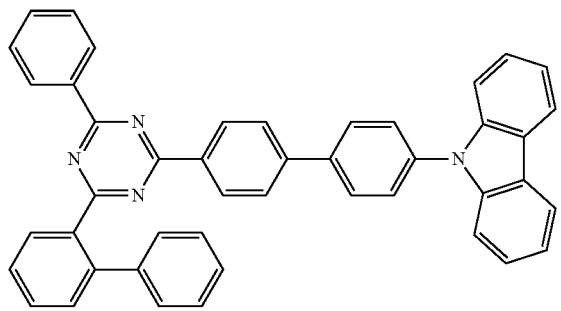
Chemical Formula 1-1-9
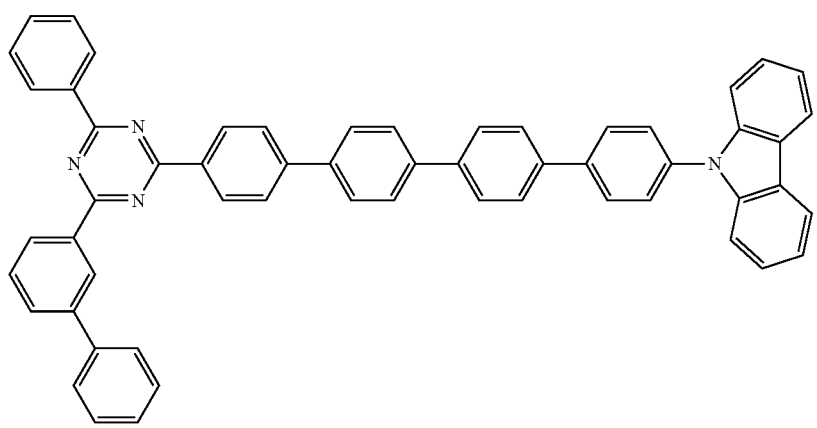

Chemical Formula 1-1-10
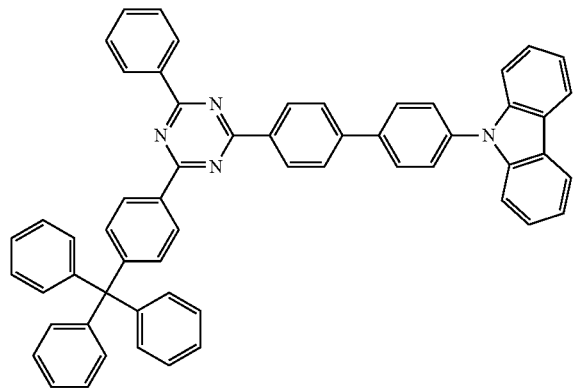
Chemical Formula 1-1-11
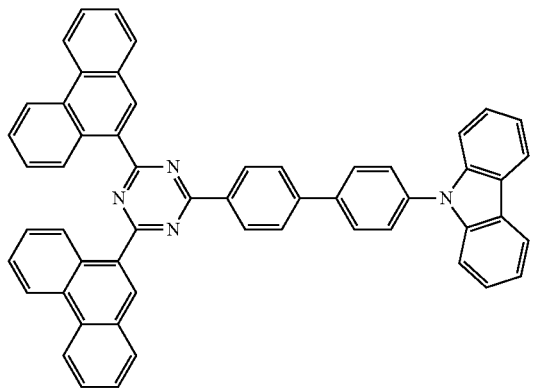
Chemical Formula 1-1-16
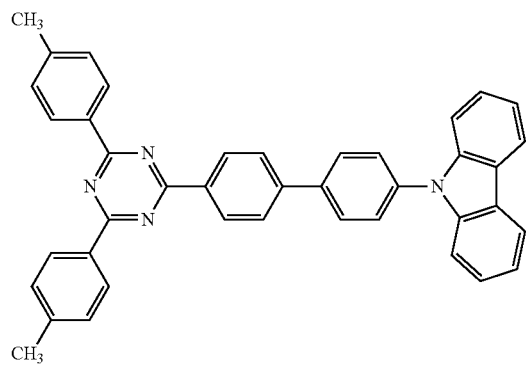
Chemical Formula 1-1-17
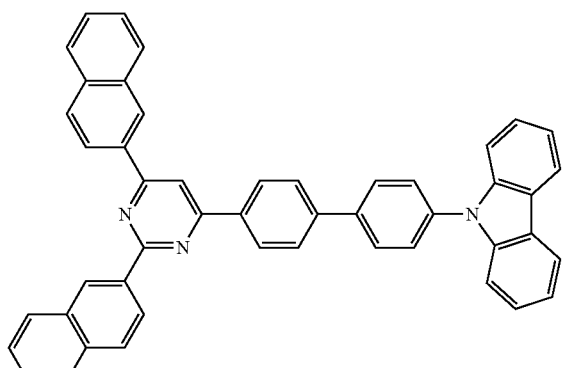
Chemical Formula 1-1-18
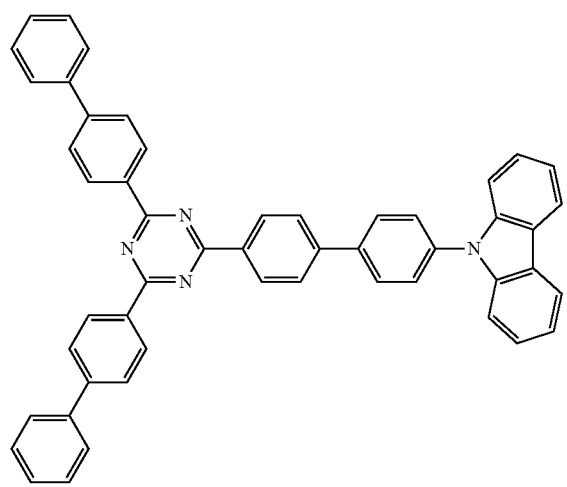
Chemical Formula 1-1-19
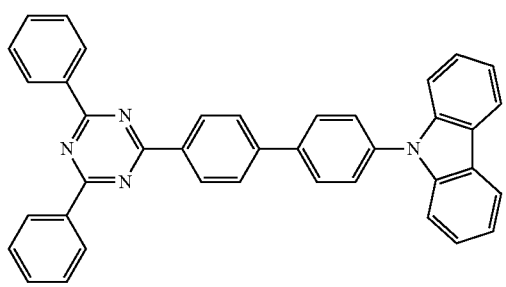

Chemical Formula 1-1-21
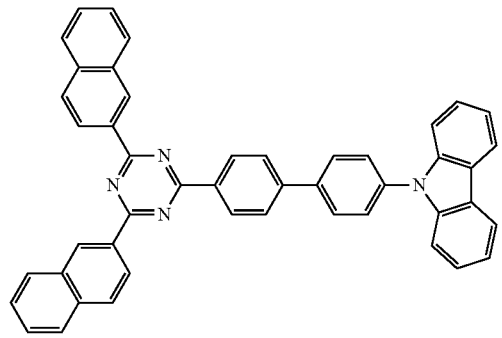
Chemical Formula 1-1-23
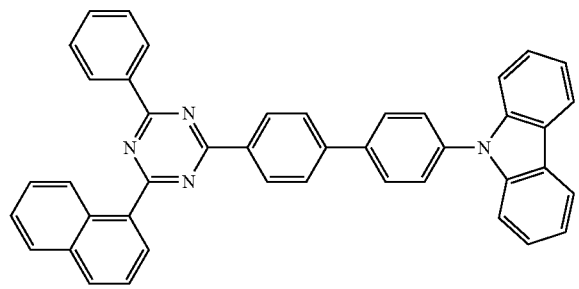
Chemical Formula 1-1-24
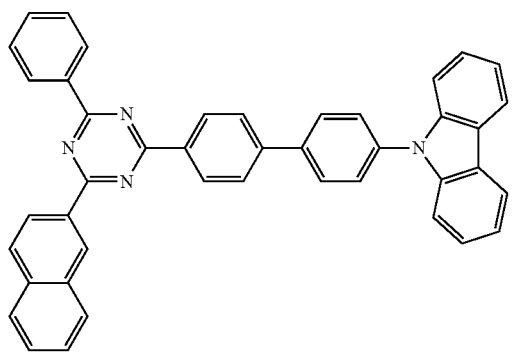
Chemical Formula 1-1-25
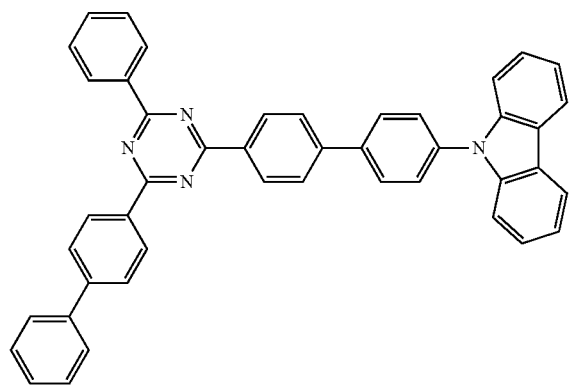
Chemical Formula 1-1-27
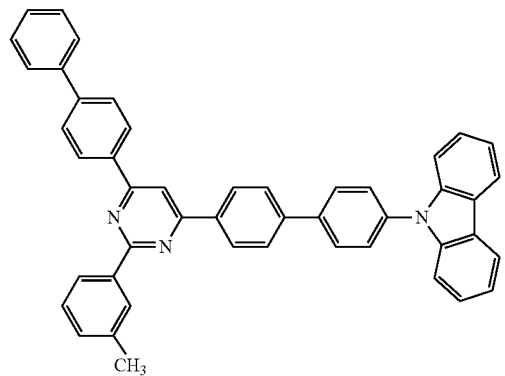

Chemical Formula 1-1-28
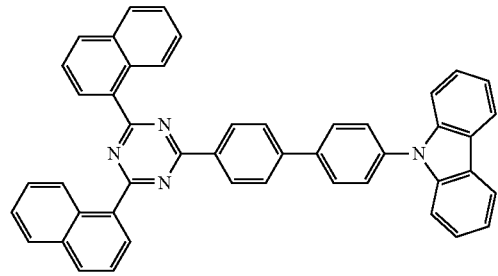
Chemical Formula 1-1-32
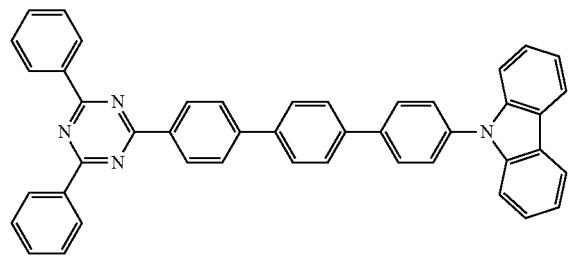
Chemical Formula 1-1-33
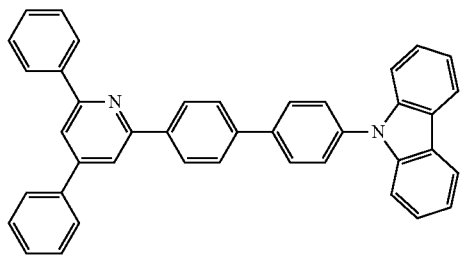
Chemical Formula 1-1-35
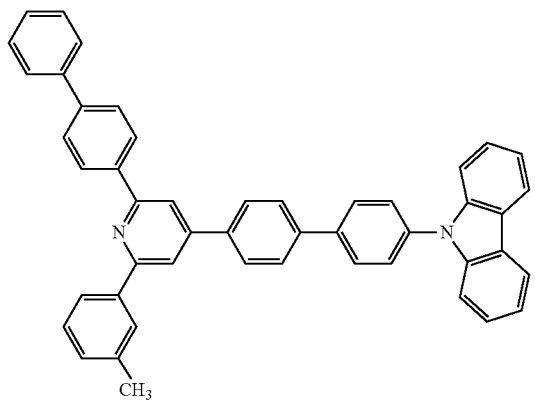
Chemical Formula 1-1-37
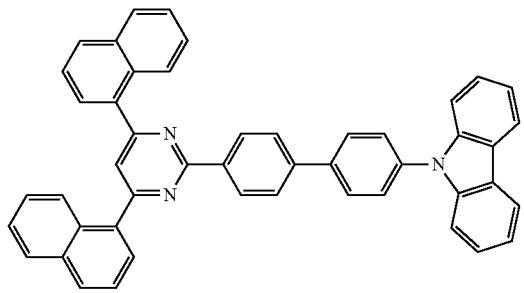

-continued
Chemical Formula 1-2-1
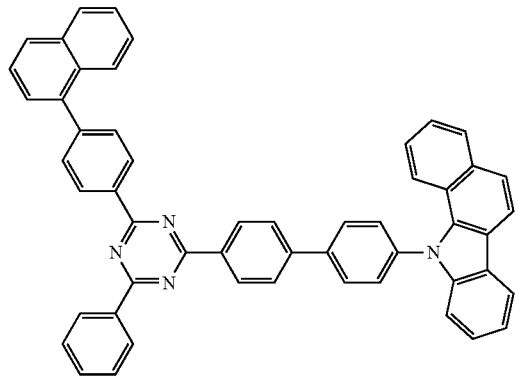
Chemical Formula 1-2-2
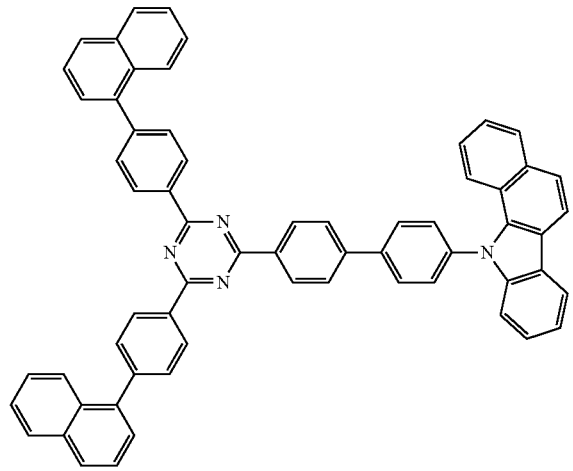
Chemical Formula 1-2-5
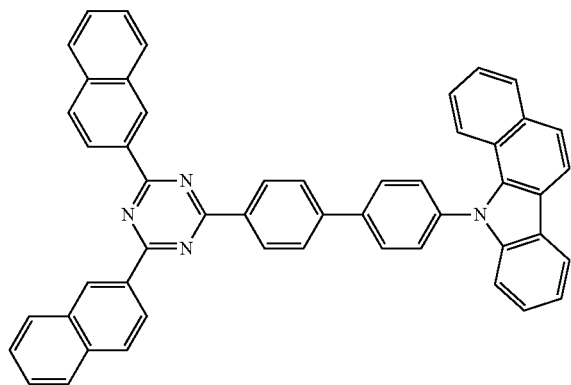
Chemical Formula 1-2-6
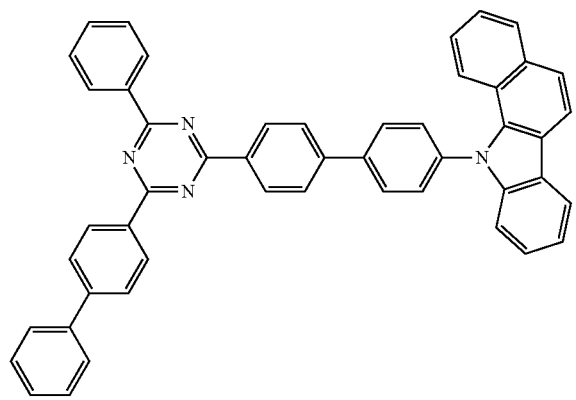
Chemical Formula 1-2-7
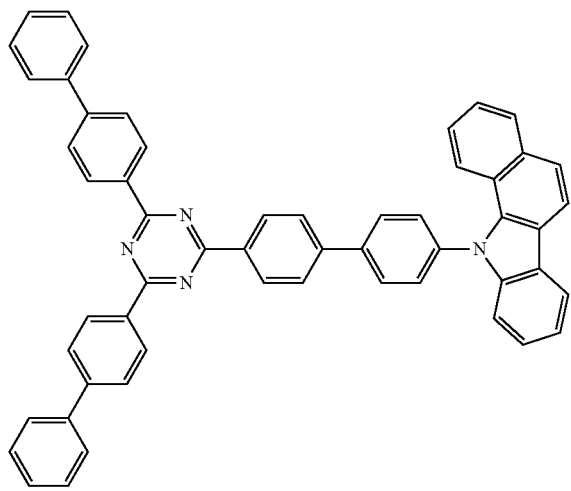
Chemical Formula 1-2-8
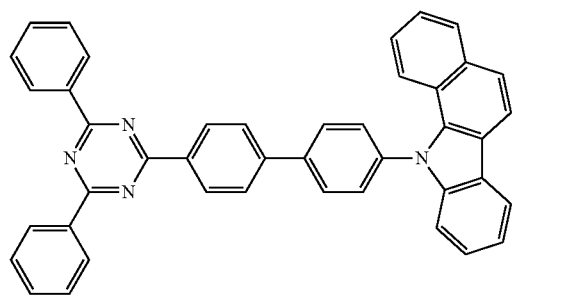

-continued
Chemical Formula 1-2-7
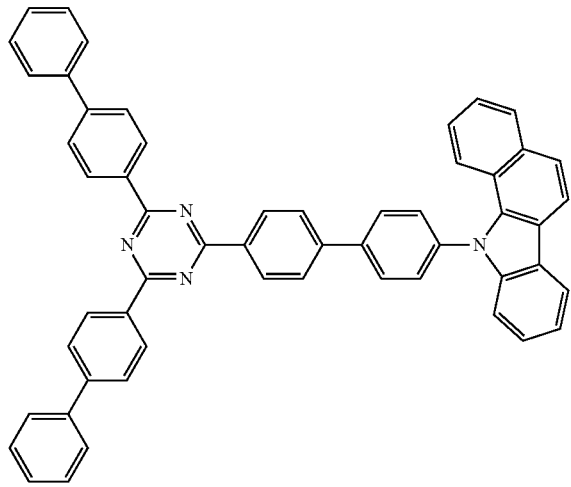
Chemical Formula 1-2-8
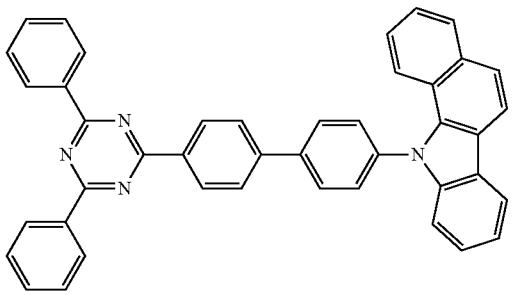
Chemical Formula 1-3-1
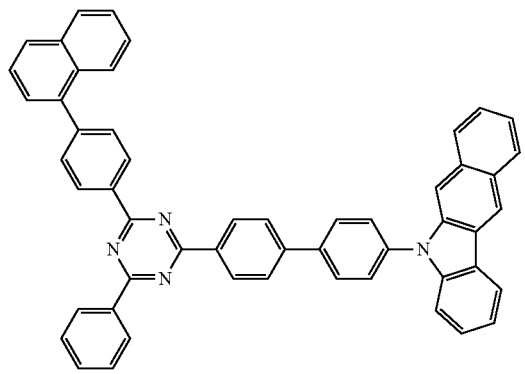
Chemical Formula 1-3-2
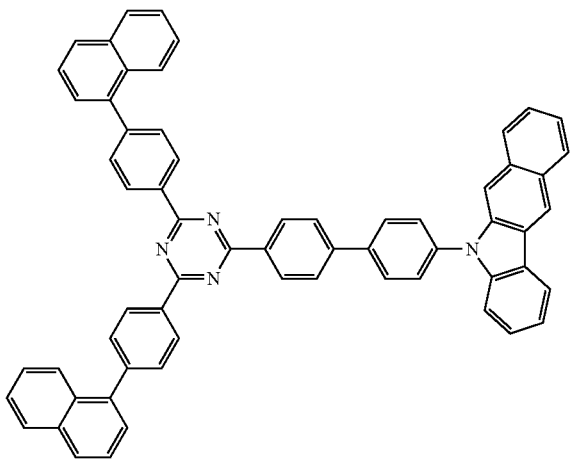
Chemical Formula 1-3-5
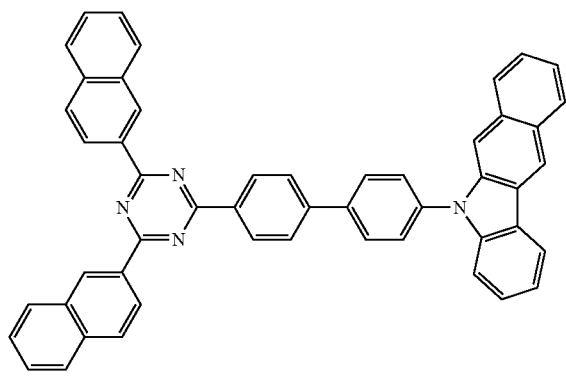
Chemical Formula 1-3-6
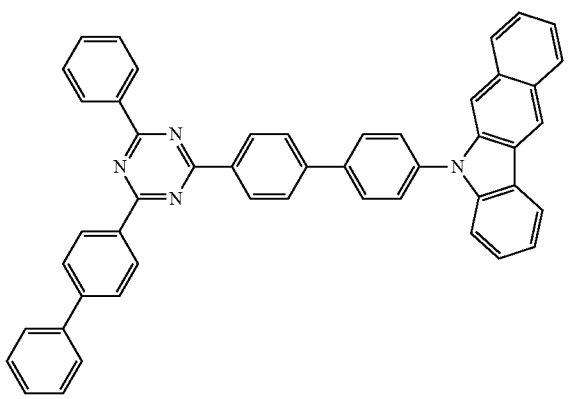

Chemical Formula 1-3-7
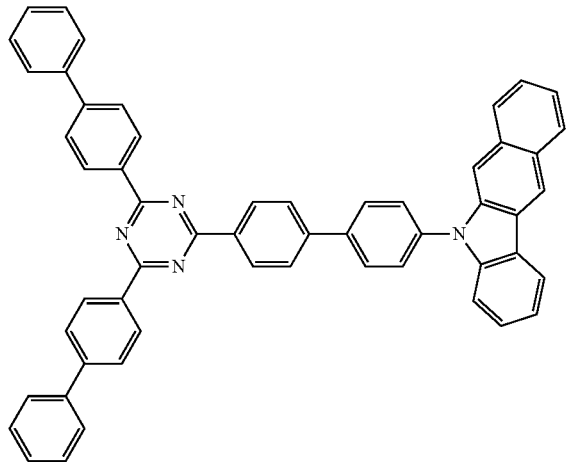
Chemical Formula 1-3-8
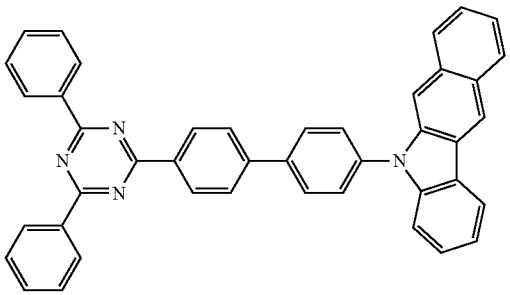
Chemical Formula 1-4-1
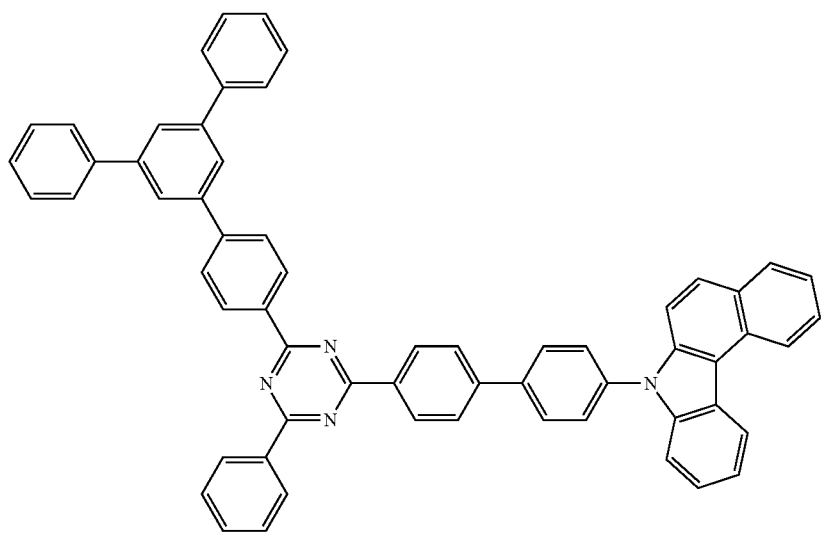
Chemical Formula 1-4-2
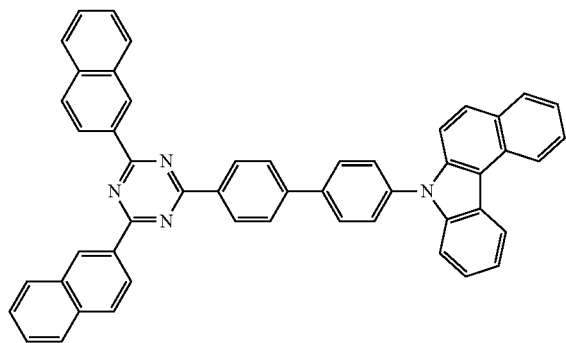
Chemical Formula 1-4-3
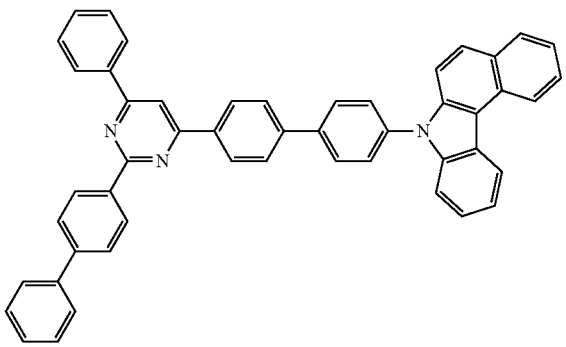

Chemical Formula 1-4-4

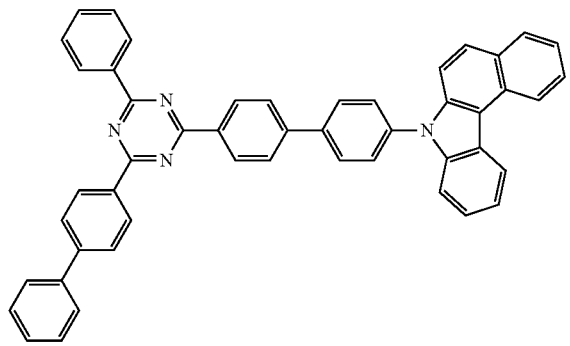

Chemical Formula 1-4-5

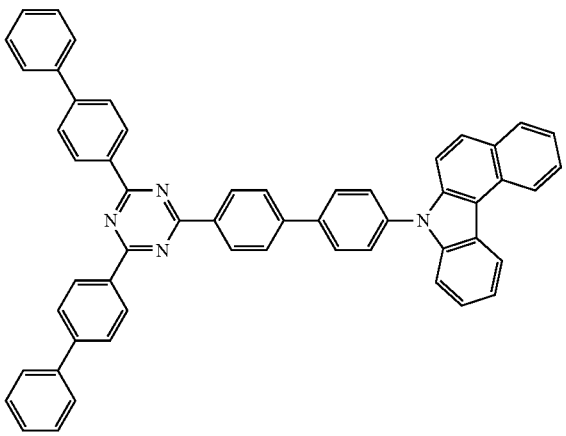

Chemical Formula 1-4-8

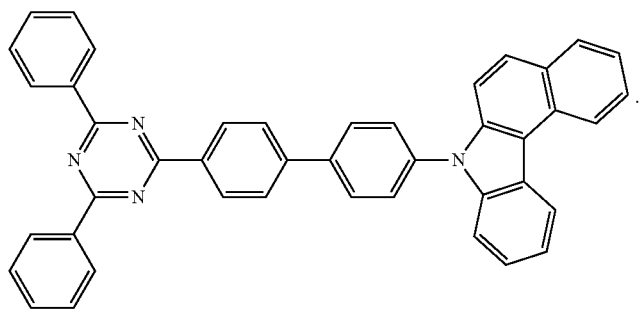

Chemical Formula 1-4-8

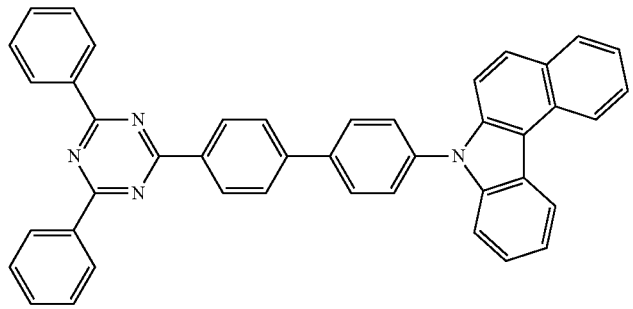

7. The organic light emitting diode of claim 1, wherein hole mobility of the compound represented by Chemical Formula 2 is $5 \times 10^{-6}$ cm$^2$/Vs or more.

8. The organic light emitting diode of claim 1, wherein Ar3 and Ar4 are the same as or different from each other, and are each independently a substituted or unsubstituted phenyl group; a substituted or unsubstituted biphenyl group; or a substituted or unsubstituted fluorenyl group.

9. The organic light emitting diode of claim 1, wherein L2 is a substituted or unsubstituted phenylene group; a substituted or unsubstituted biphenylene group; or a substituted or unsubstituted naphthalene group, or n is 0.

10. The organic light emitting diode of claim 1, wherein Y1 and Y2 are the same as or different from each other, and are each independently a substituted or unsubstituted alkyl group having 1 to 10 carbon atoms; or a substituted or unsubstituted phenyl group, or are bonded to each other to form a substituted or unsubstituted fluorene structure.

11. The organic light emitting diode of claim 1, wherein the compound represented by Chemical Formula 2 is represented by any one of the following compounds:

Chemical Formula 2-1
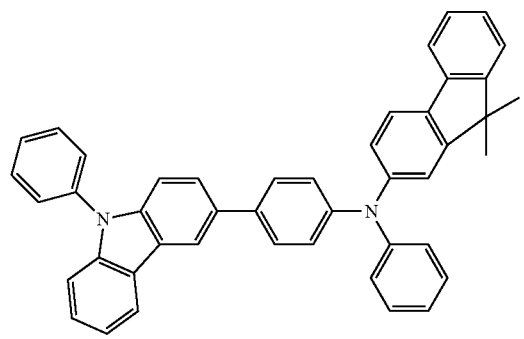
Chemical Formula 2-2
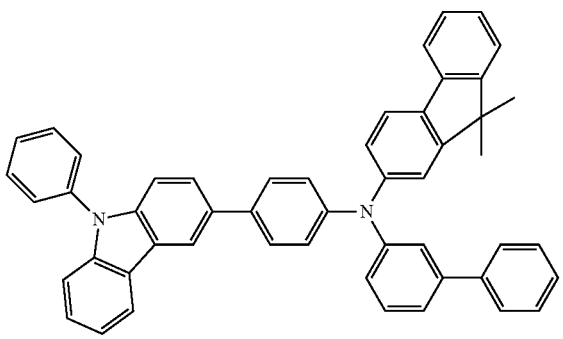
Chemical Formula 2-3
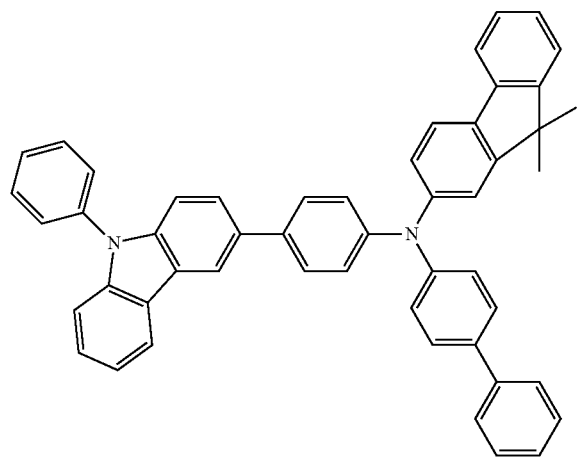
Chemical Formula 2-5
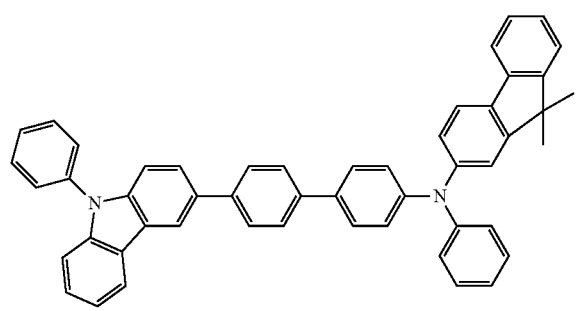
Chemical Formula 2-6
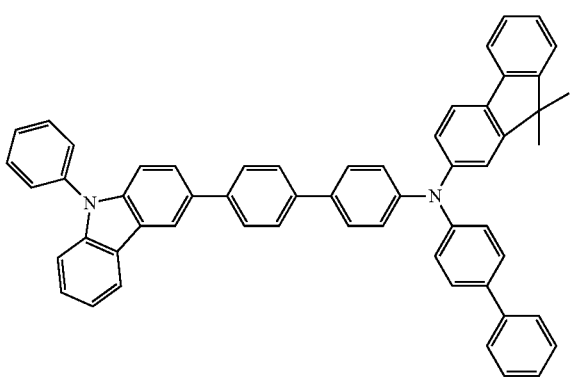
Chemical Formula 2-7
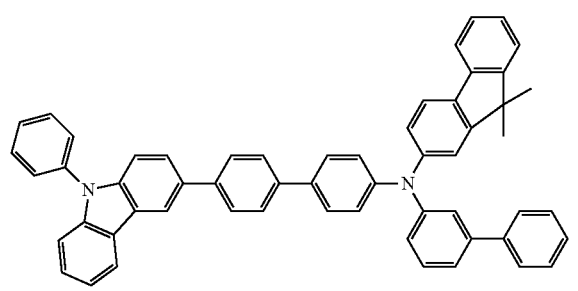

Chemical Formula 2-9
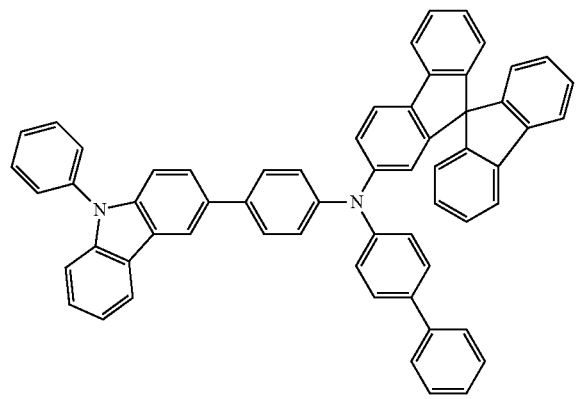
Chemical Formula 2-10
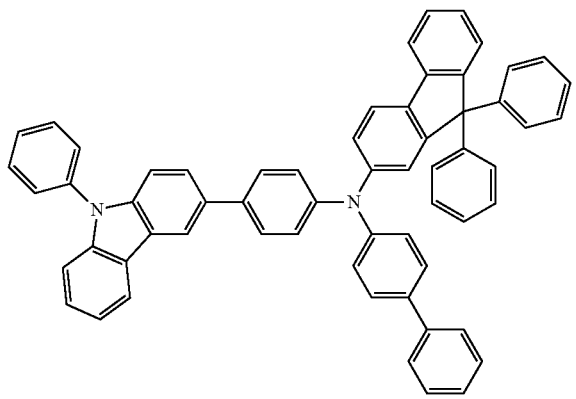
Chemical Formula 2-12
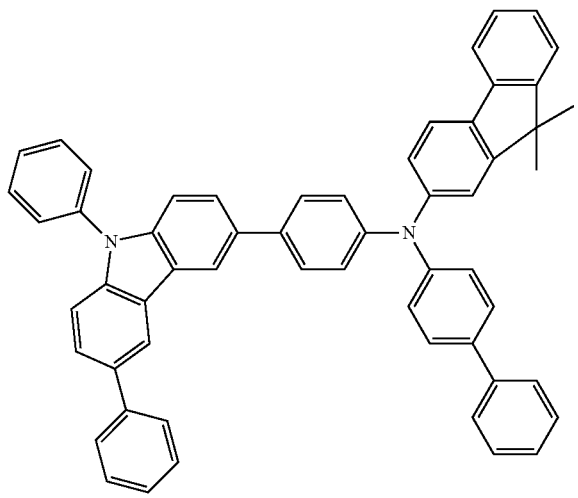
Chemical Formula 2-13
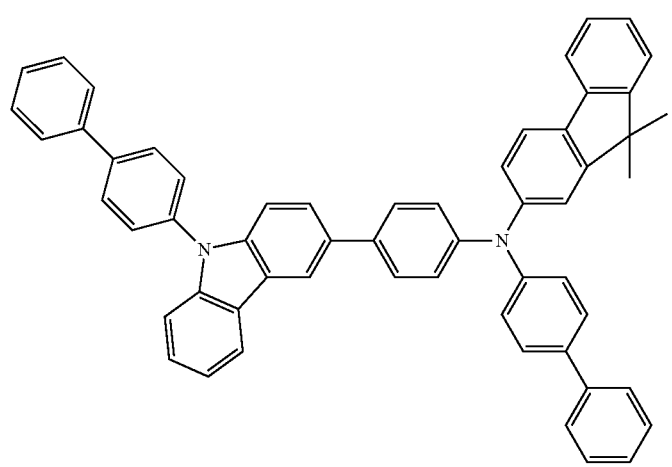

Chemical Formula 2-14
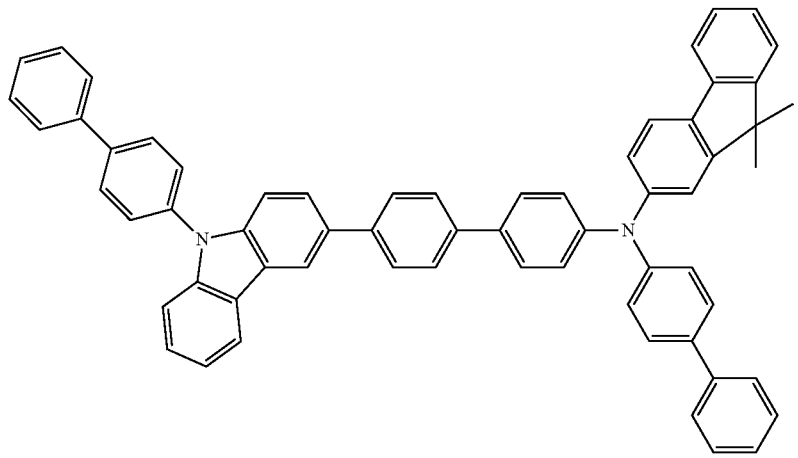
Chemical Formula 2-15
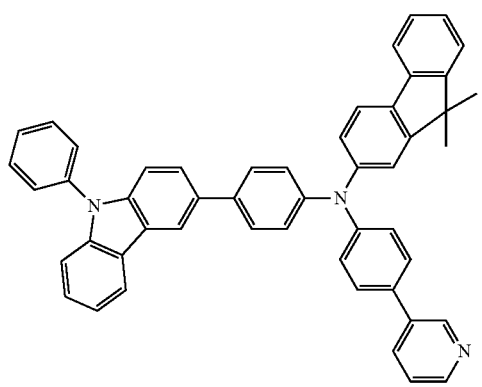
Chemical Formula 2-16
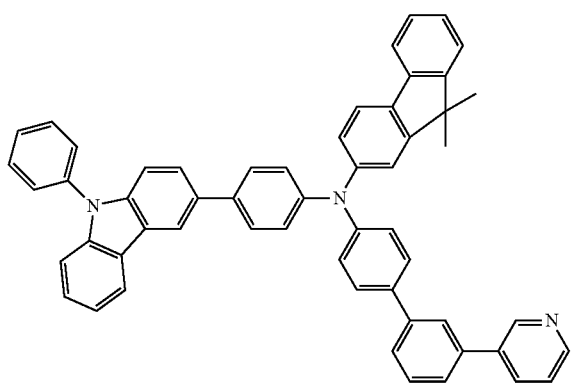
Chemical Formula 2-17
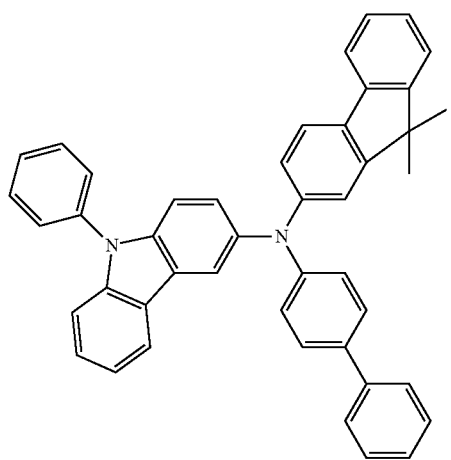

-continued
Chemical Formula 2-19
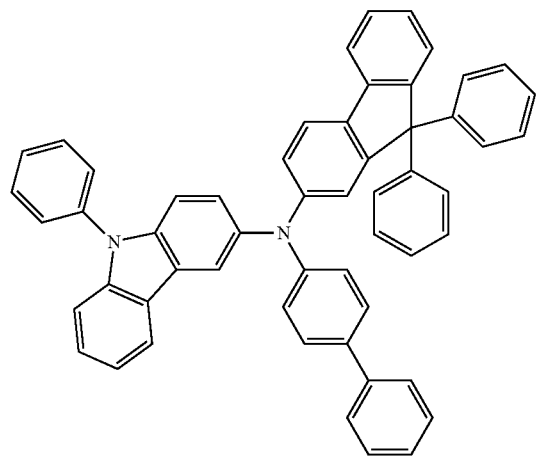
Chemical Formula 2-20
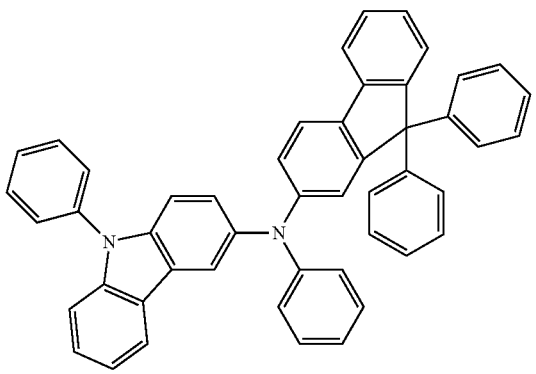
Chemical Formula 2-21
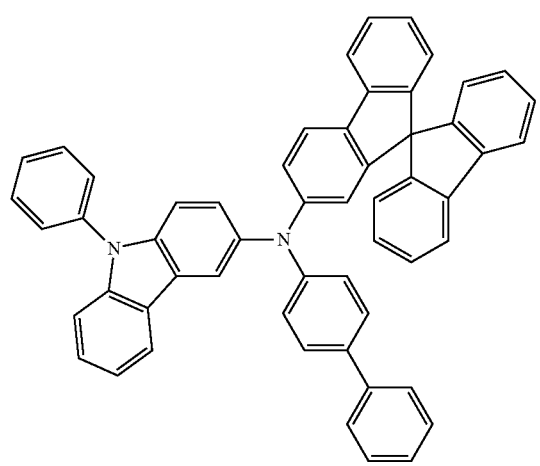
Chemical Formula 2-22
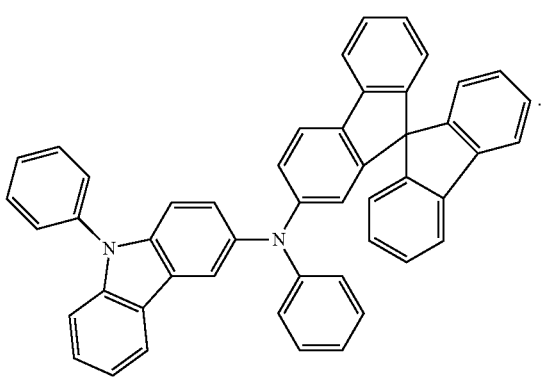
* * * * *